United States Patent
Takemoto

(10) Patent No.: US 11,096,649 B2
(45) Date of Patent: Aug. 24, 2021

(54) MEDICAL IMAGE DIAGNOSTIC DEVICE AND IMAGE PROCESSING METHOD

(71) Applicant: Hitachi, Ltd., Tokyo (JP)

(72) Inventor: Kazuma Takemoto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/630,611

(22) PCT Filed: Apr. 5, 2018

(86) PCT No.: PCT/JP2018/014588
§ 371 (c)(1),
(2) Date: Jan. 13, 2020

(87) PCT Pub. No.: WO2019/030975
PCT Pub. Date: Feb. 14, 2019

(65) Prior Publication Data
US 2021/0077054 A1    Mar. 18, 2021

(30) Foreign Application Priority Data
Aug. 8, 2017   (JP) .............................. JP2017-153011

(51) Int. Cl.
*G06T 7/00*    (2017.01)
*A61B 6/00*    (2006.01)
(Continued)

(52) U.S. Cl.
CPC .............. *A61B 6/545* (2013.01); *A61B 6/032* (2013.01); *A61B 6/0407* (2013.01); *A61B 6/40* (2013.01);
(Continued)

(58) Field of Classification Search
CPC .. G01N 2035/00326; A61B 6/06; A61B 6/08; A61B 6/54; A61N 5/1045; G02B 27/09;
(Continued)

(56) References Cited

U.S. PATENT DOCUMENTS

2011/0280366 A1   11/2011   Maeda
2012/0213326 A1    8/2012   Walker
(Continued)

FOREIGN PATENT DOCUMENTS

JP   2012-000448 A   1/2012
JP   2014-128656 A   7/2014
(Continued)

OTHER PUBLICATIONS

International Search Report with English translation and Written Opinion issued in corresponding application No. PCT/JP2018/014588 dated Jul. 3, 2018.

*Primary Examiner* — Don K Wong
(74) *Attorney, Agent, or Firm* — Foley & Lardner LLP

(57) ABSTRACT

With regard to a setting reference for X-ray irradiation range and image generation range, which differs by hospital or technician, a structure to automatically set a desired X-ray irradiation range and an image generation range infallibly, is provided. In an X-ray CT apparatus, a scan range automatic setting unit extracts an inspection target as an arbitrary body part designated by an operator before inspection from a positioning image, and generates an extraction region range including it. The operator sets an arbitrary margin value by line operation or numerical input using a GUI with respect to the extraction region range (S104). The scan range automatic setting unit generates and stores a range setting pattern in which the inspection target and the margin value are made to correspond to each other (S105), and links the range setting pattern to an inspection protocol (S106). Then immediately after positioning-image image sensing (S109), the scan range automatic setting unit extracts the inspection target from the positioning image (S112), and automatically sets a scan range, in accordance with the range setting pattern made to correspond to the inspection target and linked to the inspection protocol (S114).

12 Claims, 21 Drawing Sheets

(51) Int. Cl.
 *A61B 6/03* (2006.01)
 *A61B 6/04* (2006.01)
(52) U.S. Cl.
 CPC ............... *A61B 6/42* (2013.01); *A61B 6/465* (2013.01); *A61B 6/467* (2013.01); *A61B 6/503* (2013.01)
(58) Field of Classification Search
 CPC ............ G02B 27/0916; G02B 27/0933; G02B 27/0988; G21K 1/02; G21K 1/025; G21K 1/04; G21K 1/043; G21K 1/046
 See application file for complete search history.

(56) References Cited

U.S. PATENT DOCUMENTS

| | | |
|---|---|---|
| 2014/0185740 A1 | 7/2014 | Chen |
| 2015/0228071 A1* | 8/2015 | Jockel .................. H04N 13/204 382/132 |
| 2015/0297157 A1 | 10/2015 | Mukumoto |
| 2015/0297166 A1 | 10/2015 | Goto |
| 2018/0116622 A1* | 5/2018 | Jan ......................... G01B 17/02 |

FOREIGN PATENT DOCUMENTS

| | | |
|---|---|---|
| JP | 2015-213748 A | 12/2015 |
| JP | 2015-213749 A | 12/2015 |

\* cited by examiner

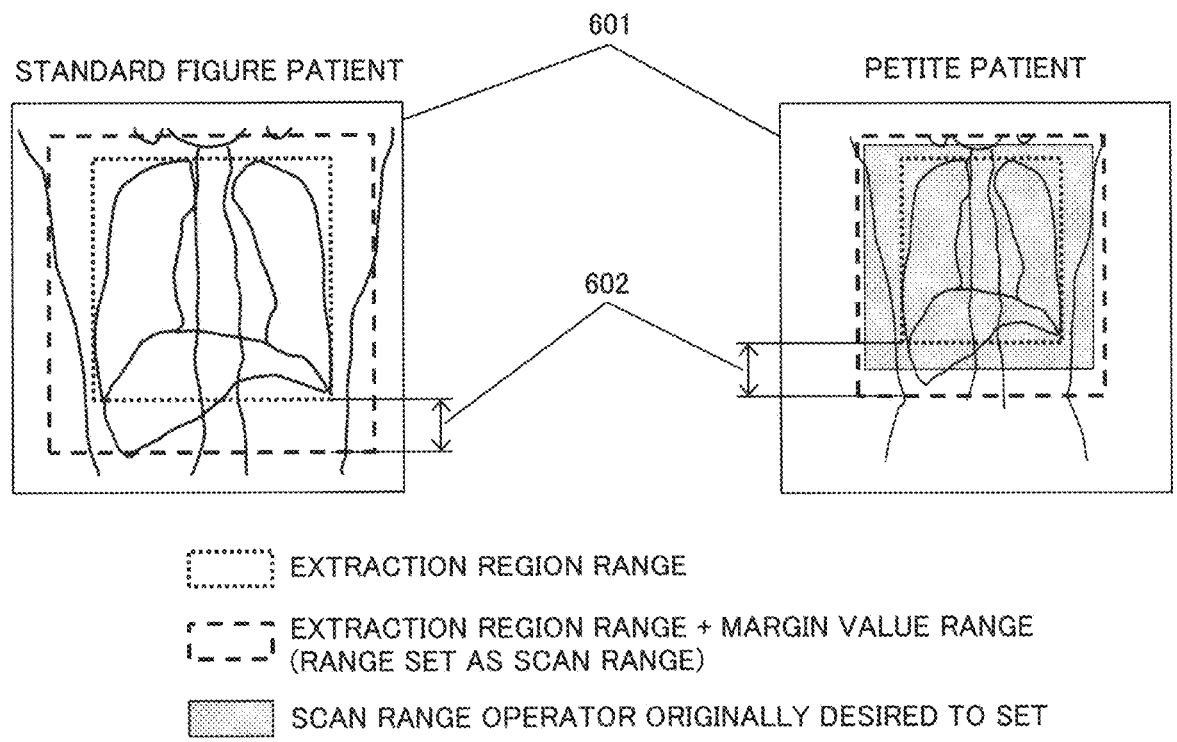

| TABLE HEIGHT [mm] | IMAGE MAGNIFICATION | ... |
|---|---|---|
| ⋮ | ⋮ | ... |
| 220 | 1.2 | ... |
| 210 | 1.1 | ... |
| 200 | 1.0 | ... |
| 190 | 0.9 | ... |
| 180 | 0.8 | ... |
| ⋮ | ⋮ | ⋮ |

1001

(b)

| TABLE HEIGHT [mm] | IMAGE MAGNIFICATION | ... |
|---|---|---|
| ⋮ | ⋮ | ... |
| 220 | 0.8 | ... |
| 210 | 0.9 | ... |
| 200 | 1.0 | ... |
| 190 | 1.1 | ... |
| 180 | 1.2 | ... |
| ⋮ | ⋮ | ⋮ |

1002

MEDICAL IMAGE DIAGNOSTIC DEVICE AND IMAGE PROCESSING METHOD

TECHNICAL FIELD

The present invention relates to a medical image diagnostic device, and more particularly, to a technique of setting an X-ray irradiation range and an image generation range in actual image sensing using a positioning image obtained before actual image sensing.

BACKGROUND ART

Medical image diagnostic devices are essential for modern medicine, and as one of these devices, an X-ray CT (Computed Tomography) apparatus is known. The X-ray CT apparatus reconstructs a tomographic image of a patient with projection data from plural angles, obtained by circulating an X-ray source to irradiate the patient with an X-ray and an X-ray detector to detect the exposure dose of the X-ray transmitted through the patient, around the patient, and displays the reconstructed tomographic image. The image displayed with the X-ray CT apparatus describes the shapes of organs in the patient. The image is used in medical image diagnosis. As other medical image diagnostic devices, an MRI (Magnetic Resonance Imaging) device and the like are known. In the present specification, as an example, the X-ray CT apparatus will be described below.

In the X-ray CT apparatus, generally, before execution of actual image sensing, image sensing is performed on a positioning image for planning of actual sensing with respect to a patient. An operator operates a line or the like on the positioning image, to set an X-ray irradiation range and an image generation range in actual image sensing, and sets various image sensing parameters. Note that in the present specification, the X-ray irradiation range and the image generation range will be integrally referred to as a "scan range".

In actual image sensing planning, guidelines described by image sensing region and inspection purpose exist. It is possible to perform actual image sensing under image sensing conditions, unified to a certain degree, by planning actual image sensing with reference to the guidelines. Further, in the medical image diagnostic devices by respective makers, systems to previously set image sensing conditions, recommended in the guidelines and the like, as protocols, are installed. Most of the image sensing conditions are not necessarily changed upon inspection.

However, there is a limit to the actual image sensing planning utilizing the guidelines and the protocol. Particularly, in the setting of the above-described scan range, as the positioning image differs by patient, the scan range set with the protocol is inappropriate in many cases. To set an appropriate range, the operator needs experience. Accordingly, in most cases, upon inspection, it is necessary for the operator to manually set the scan range, and inaccuracy occurs in the scan range setting.

In the conventional technique as shown in PTL 1, to improve the labor and inaccuracy in the scan range setting manually performed by the operator, automatic X-ray irradiation range setting upon actual image sensing planning is attempted.

CITATION LIST

Patent Literature

PTL 1: Japanese Patent Application Laid-Open No. 2014-128656

SUMMARY OF INVENTION

Technical Problem

In the above-described conventional technique, a feature amount is extracted from a positioning image, and a range extracted with the feature amount is set as a scan range. However, the reference of scan range setting slightly differs by hospital or operator. Accordingly, in the method of setting a scan range with a uniform reference, the scan range which the operator originally desires to set is not set, and it is necessary for the operator to manually operate the scan range at last. The effect of improvement of the operator's labor and the inaccuracy of scan range setting upon inspection, as an initial purpose, is reduced.

The object of the present invention is to provide a medical image diagnostic device and an image processing method capable of, in correspondence with a scan range setting reference which differs by hospital or operator, improving the operator's labor and inaccuracy upon scan range setting.

Solution to Problem

To achieve the abovementioned object, the present invention provides a medical image diagnostic device including: a storage part that links a range setting pattern, in which an inspection target and a margin value are made to correspond to each other, to an inspection protocol, and stores the range setting pattern and the inspection protocol; and a scan range automatic setting unit that, after image sensing of a positioning image obtained by image sensing a patient, automatically sets a scan range upon inspection in accordance with the range setting pattern linked to the inspection protocol.

Further, to achieve the abovementioned, the present invention provides image processing method for a medical image diagnostic device having a storage part and a control part, including: linking, to an inspection protocol, a range setting pattern in which an inspection target and a margin value are made to correspond to each other, and storing the range setting pattern and the inspection protocol in the storage part, and after image sensing of a positioning image obtained by image sensing a patient, the control part automatically sets a scan range upon inspection in accordance with the range setting pattern linked to the inspection protocol.

Advantageous Effects of Invention

According to the present invention, it is possible to improve the operator's labor and inaccuracy upon scan range setting, in correspondence with scan range reference which differs by hospital or operator.

BRIEF DESCRIPTION OF DRAWINGS

FIG. 6 is a diagram for explaining the influence by individual differences of a patient according to Example 1.

FIG. 7 is a diagram showing an example of a margin value map according to Example 1.

FIG. 10 is a diagram showing an example of a map in which the table height and the magnification of the patient within an image are made to correspond to each other, according to Example 2.

DESCRIPTION OF EMBODIMENTS

Figure 2:
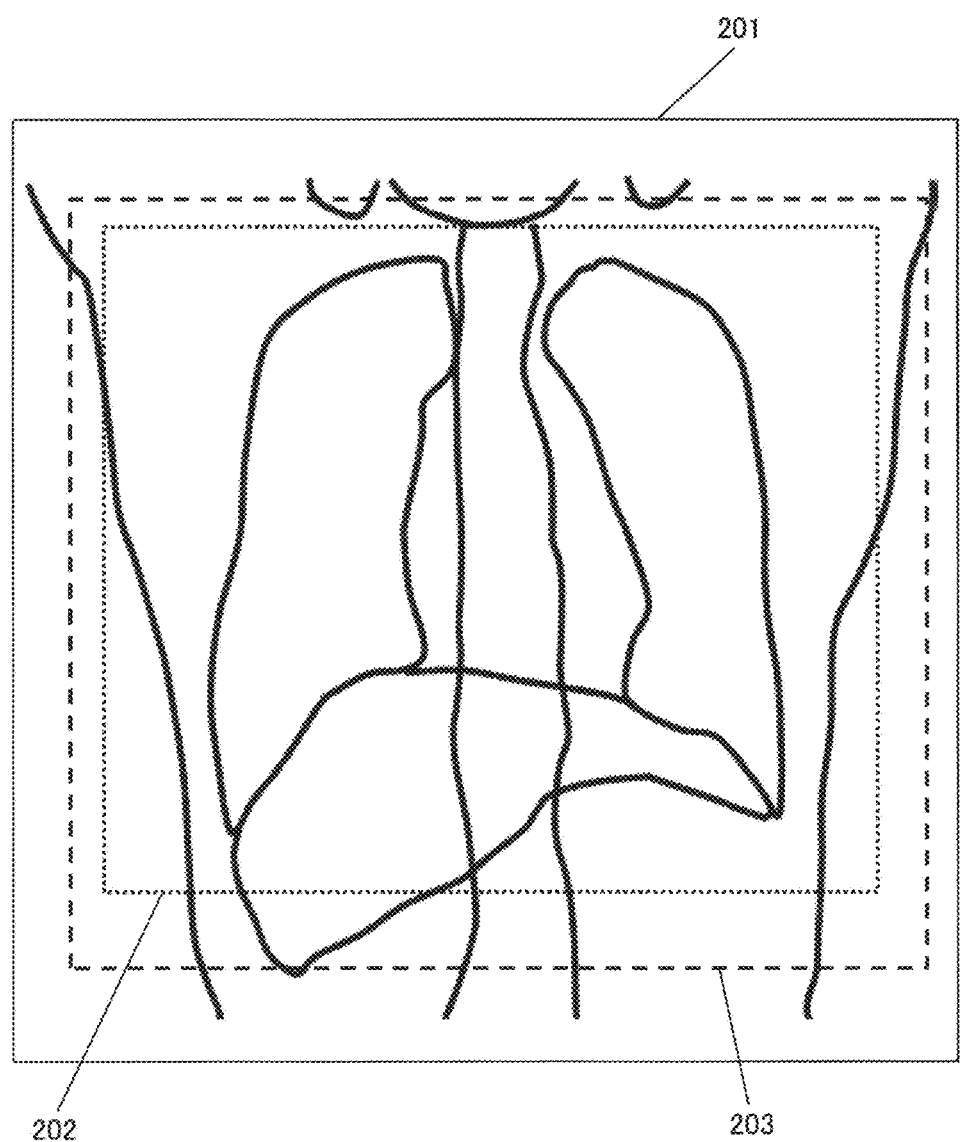
FIG. 2 is a diagram for explaining the problem of the conventional technique.

Various examples of the present invention capable of solving the above-described problem will be sequentially described. First, to assist understanding or the present invention, the object solved with the present invention will be described with the drawings. As shown in FIG. 2, in the conventional automatic setting method, in some cases, an automatically-set scan range 202 and a san range 203 which an operator originally desires to set do not correspond with each other. In this method, a feature amount is extracted from a positioning image 201, and a range based on the extracted feature amount is set as the scan range 202. However, as described above, the reference for scan range setting slightly differs by hospital or operator.

Figure 3:
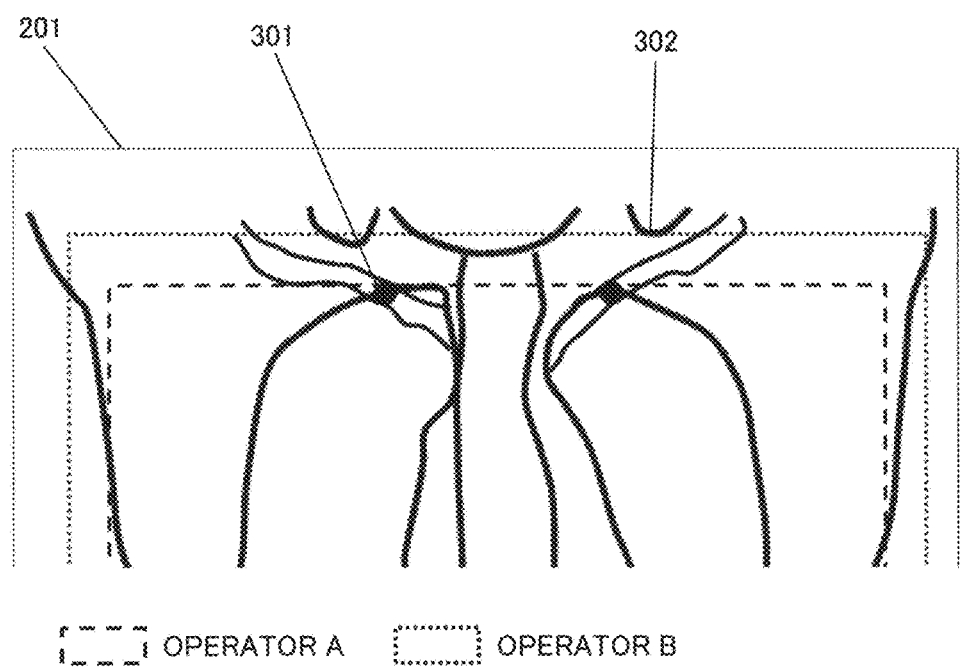
FIG. 3 is a diagram for explaining difference in reference for scan range setting by operator.

For example, FIG. 3 shows the difference in reference for setting a head-side position in a scan range in the case of image sensing a lung field for the same inspection purpose. An operator A performs scanning with an "intersection 301 between a clavicle and a rib" as a guide, and an operator B, with a "cavity 302 of a shoulder formed between a raised arm and a head" as a guide. In this case, in the method of scan range setting with a uniform reference as in the case of PTL 1, the scan range which the operator originally desires to set is not set, and it is necessary for the operator to manually adjust the scan range at last. The effect of improvement of the operator's labor and inaccuracy in scan range setting, as the first purpose, is small.

Example 1

Figure 1:
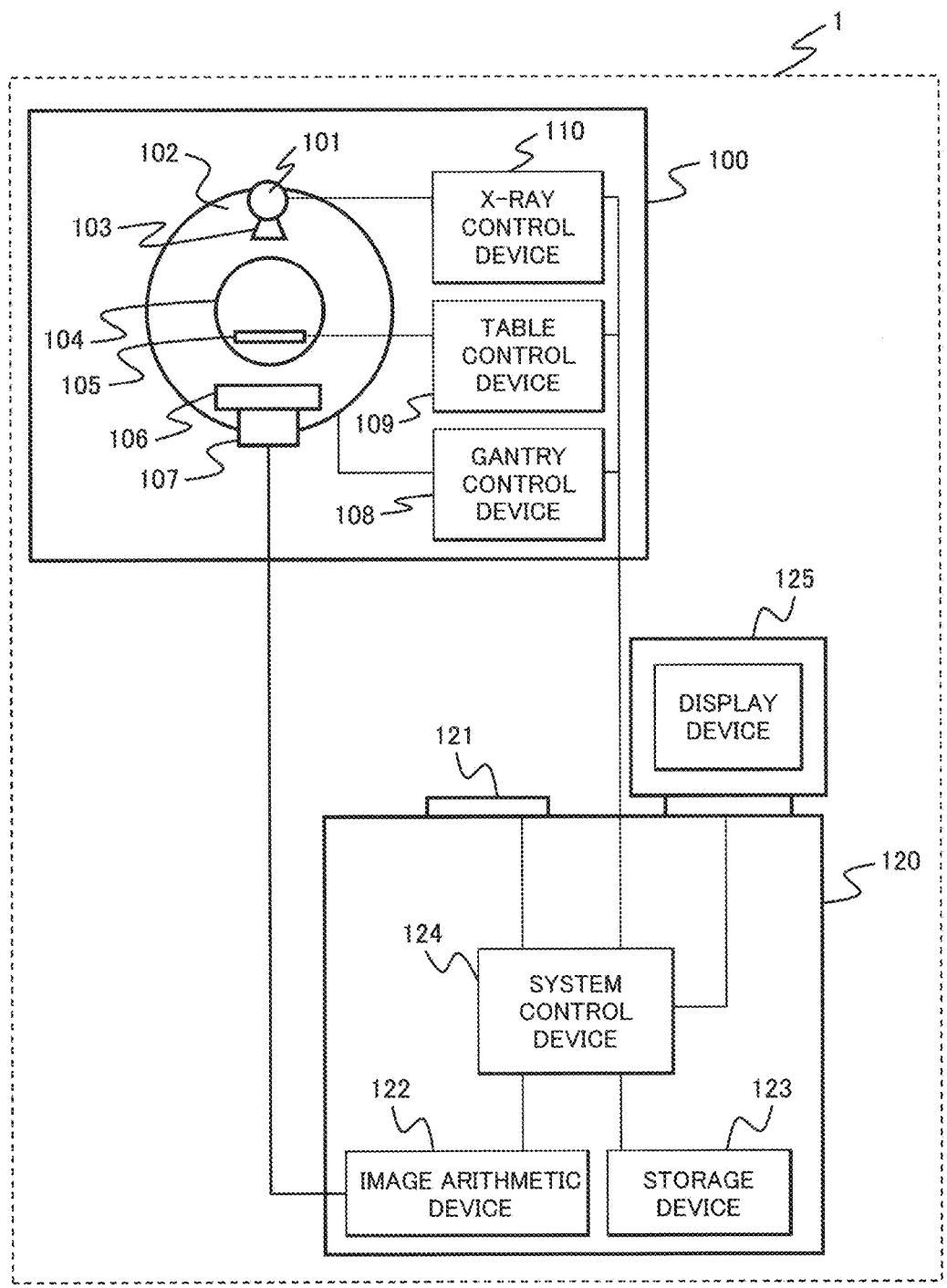
FIG. 1 is a diagram for explaining an example of the entire configuration of an X-ray CT apparatus according to respective examples.

First, an example of the entire configuration of an X-ray CT apparatus to which the respective examples are applied will be described by using FIG. 1.

An X-ray CT apparatus 1 is provided with a scan gantry part 100 and a console 120. The scan gantry part 100 is provided with an X-ray tube 101, a rotary disc 102, a collimator 103, an X-ray detector 106, a data collection device 107, a table 105, a gantry control device 108, a table control device 109, and an X-ray control device 110.

The X-ray tube 101 is a device to irradiate a patient placed on the table 105 with an X-ray. The collimator 103 is a device to limit a radiation range of the X-ray irradiated from the X-ray tube 101. The rotary disc 102 is provided with an opening 104 which the patient placed on the table 105 enters. The rotary disc 102 is also provided with the X-ray tube 101 and an X-ray detector 106, and rotates around the patient. The X-ray detector 106 is a device oppositely provided to the X-ray tube 101, to measure the spatial distribution of transmission X-ray by detecting the X-ray transmitted through the patient. The X-ray detector 106 has a large number of X-ray detection elements arrayed in a rotation direction of the rotary disc 102 or two-dimensionally arrayed in the rotation direction and a rotation axis direction of the rotary disc 102. The data collection device 107 is a device to collect an X-ray exposure dose detected with the X-ray detector 106 as digital data. The gantry control device 108 is a device to control rotation of the rotary disc 102. The table control device 109 is a device to control up-and-down and back-and-forth movements of the table 105. The X-ray control device 110 is a device to control electric power inputted into the X-ray tube 101.

The console 120 is provided with an input device 121, an image arithmetic device 122, a display device 125, a storage device 123, and a system control device 124. The console 120 as above can be realized with a personal computer (PC) having a normal computer configuration, a server, or the like. The input device 121 is a device to input the patient's name, inspection date and time, image sensing conditions, and the like. More particularly, the input device 121 is a keyboard, a pointing device or the like. The image arithmetic device 122 is a device to perform arithmetic processing on measurement data transmitted from the data collection device 107 to perform CT image reconstruction. The display device 125 is a device to display a CT image generated with the image arithmetic device 122. More particularly, the display device 125 is a CRT (Cathode-Ray Tube), a liquid crystal display, or the like. The storage device 123 is a device to store data collected with the data collection device 107 and image data of the CT image generated with the image arithmetic device 122. More particularly, the storage device 123 is an HDD (Hard Disk Drive) or the like. The system control device 124 is a control part of the entire apparatus to control these devices and the gantry control device 108, the table control device 109, and the X-ray control device 110.

When the X-ray control device 110 controls electric power inputted into the X-ray tube 101 based on image sensing conditions such as a scan range, especially an X-ray tube voltage and an X-ray tube current, inputted from the input device 121, the X-ray tube 101 irradiates the patient with an X-ray corresponding to the image sensing conditions. The X-ray detector 106 detects the X-ray irradiated from the X-ray tube 101 and transmitted through the patient with the large number of X-ray detection elements, and measures the transmission X-ray distribution. The rotary disc 102, controlled with the gantry control device 108, rotates based on the image sensing conditions, especially a rotational speed or the like, inputted from the input device 121. The table 105, controlled with the table control device 109, operates based on the image sensing conditions, especially a helical pitch, inputted from the input device 121.

By repetition of X-ray irradiation from the X-ray tube 101 and measurement of transmission X-ray distribution with the X-ray detector 106 along with the rotation of the rotary disc 102, projection data from various angles is obtained. The obtained projection data from various angles is transmitted to the image arithmetic device 122. The image arithmetic device 122 performs reverse projection processing on the transmitted projection data from various angles, to reconstruct a CT image.

The CT image obtained by the reconstruction is displayed on the display device 125.

Next, processing for scan range setting in the X-ray CT apparatus according to Example 1 will be described along the flowchart of FIG. 4. The X-ray CT apparatus to execute the flowchart is provided with a storage part to link a range setting pattern, in which an inspection target and a margin value are made to correspond to each other, to an inspection protocol, and store the range setting pattern and the inspection protocol, and a scan range automatic setting unit to, after image sensing on a positioning image obtained by image sensing a patient, automatically set a scan range upon inspection, in accordance with the range setting pattern linked to the inspection protocol.

As shown in the figure, the scan range setting flow divides into pre-inspection (S101 to S107) and post-inspection (S108 to S114). Note that the processing entity of this flowchart is the operator, the image arithmetic device 122, the system control device 124, and the like. The processing is performed by program execution with a central processing unit (CPU) of the PC constructing the image arithmetic device 122 and the system control device 124. With this processing, scan range automatic setting processing with the scan range automatic setting unit upon inspection is realized. The processing is, for example, extracting an inspection target designated by the operator from a positioning image; generating an extraction region range including this inspection target; generating a range setting pattern in which a margin value with an arbitrary width, determined by the operator by using a GUI, is made to correspond to the extraction region range; and linking the generated range setting pattern to an inspection protocol. That is, the scan range automatic setting unit controls the display device 125 as a display unit to display the positioning image and the range setting pattern based on the margin value inputted from the input unit. Further, as described later, the scan range automatic setting unit controls the display unit to display a list of range setting patterns stored in the storage part.

(Step S101) Range Setting Pattern Generation

The operator performs range setting pattern generation in the pre-inspection flow. As described later, this range setting pattern indicates a range set as a scan range upon inspection. It is desirable that the operator sets the range setting pattern on the GUI. For example, the range setting pattern is generated on a range setting pattern generation screen 501 in FIG. 5 as an example of the GUI. As shown in the right side of the lower part in FIG. 5, a positioning image 503, a line indicating the position of an extraction region range 504 on the positioning image 503, and a line indicating the position of a range 505 where the extraction region range and margin values are added as a range setting pattern, are displayed on the generation screen. That is, by displaying the line indicating the position of the range 505 of the range setting pattern set as a scan range upon inspection on the GUI, the operator can easily imagine the scan range upon inspection. With this configuration of the present example, since it is possible to visually grasp the guide of the range extracted upon inspection, it is possible to increase the accuracy of matching to the scan range which the operator desires to set upon inspection.

Note that for example, the positioning image 503 displayed on the screen may be the image of a human body phantom imitating the human body anatomical structure, or may be the positioning image of the patient obtained in the past inspection. The line indicating the position of the extraction region range 504 is extracted by applying an arbitrary extraction algorithm to the positioning image 503. The extraction method may be a publicly-known method. For generation of range setting pattern in which the inspection target and the margin values are made to correspond to each other, the operator designates a pattern name of the range setting pattern, an inspection target, an application location, margin values, and the like, with a range setting pattern details setting unit 502. Hereinbelow S102 to S105 as main steps related to the range setting pattern generation will be described in detail.

(Step S102) Designation of Inspection Target

First, the operator designates a pattern name such as "lung field A" which has been arbitrarily set, thus designates an inspection target of the range setting pattern by an arbitrary method. For example, a method of previously associating a location name with a position in the body, and designating "lung field" or the like may be used. Further, a method of designating an arbitrary part with respect to a human body imitation figure may be used.

Further, it is desirable that in correspondence with the designated inspection target, the positioning image is changed to an image appropriate to the inspection target. Otherwise, a whole-body positioning image may always be displayed. Further, plural inspection targets may be designated with respect to one range setting pattern.

(Step S103) Setting of Application Location

The operator sets whether automatic setting is applied by item to determine a scan range (hereinbelow, range parameter). The range parameter is, e.g., a head side position, a foot side position, an FOV (Field of View), and FOV center and the like, shown in the left side of the lower part in FIG. 5. Apply/not apply of automatic setting (ON/OFF) and the like are set with a range setting pattern details setting unit 502. In medical image diagnosis, in comparative interpretation with a past image-sensed image, in some cases, the deterioration of interpretation is prevented by fixing only the FOV with a designated value. The present example having the configuration is applicable to such case, thus has high versatility.

Regarding the values applied upon inspection, as a range parameter set to "applied (ON in FIG. 5)", a value obtained by adding an extraction region range and a margin value is applied as an image sensing condition, and is projected in the range setting pattern. As a range parameter set to "not applied (OFF in FIG. 5)", e.g., a form to set a default value is prepared on the range setting pattern generation screen in FIG. 5, and the value input in the form may be used. Otherwise, it may be configured such that an inspection protocol is previously registered, and the set value is used.

(Step S104) Designation of Margin Value

Figure 5:
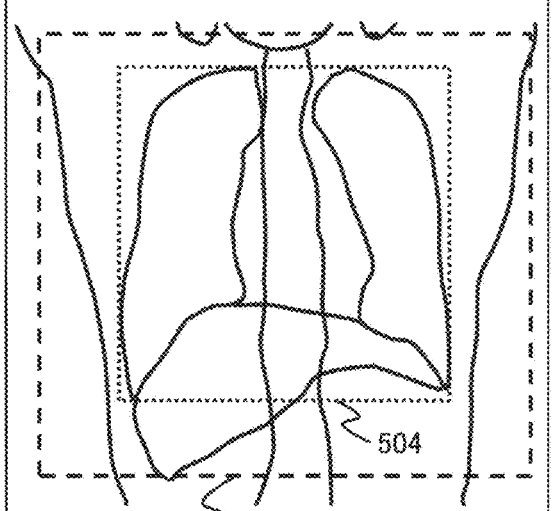
FIG. 5 is a diagram showing an example of a range setting pattern generation screen where an inspection target and a margin value are made to correspond to each other according to Example 1.

The operator designates a margin value by range parameter with respect to the position of the extraction region range. The margin value is a value of a margin in the range 505 set as a scan range upon inspection. For example, as shown in FIG. 5, the margin value may be designated by numeral input with the range setting pattern details setting unit 502, otherwise may be designated by operating a line indicating the range 505 displayed on the positioning image with a mouse. The unit of the margin value may be the unit of image sensing position (millimeter or the like), or may be the number of pixels on the image.

(Step S105) Storage of Range Setting Pattern

The range setting pattern in which the extraction region range generated with the contents designated by the operator and the margin values are made to correspond to each other, at the above step, is stored in the storage part such as the storage device 123. As shown in the upper part of FIG. 5, the plural range setting patterns stored and accumulated in the storage part may be displayed as a list 506. The list 506 displays the respective pattern names, ON/OFF, margin values corresponding to the inspection targets, respectively. The operator can perform storage, new pattern generation, deletion, and termination of generation, of the range setting pattern, by arbitrarily utilizing buttons on the GUI screen.

(Step S106) Generation of Margin Value Map

At this step, to further improve the effect with the configuration of the present example, a margin value map to adjust the margin values by utilizing information of the patient or the like is generated. Even when the range setting pattern as the range 505, obtained by adding the extraction range generated at steps S101 to S105 and the margin values, is applied to the scan range upon inspection, in some cases, it is difficult to make the range setting pattern follow the individual differences of the patient. Accordingly, the influence by the individual differences is eliminated by adjusting the margin values based on patient information which can be the individual differences of the patient. For example, the individual differences of the patient include a physique difference.

As shown in FIG. 6, the size within a positioning image 601 differs in many cases between a standard figure patient shown on the left side of the figure and a petite patient shown on the right side. Accordingly, when the same margin value 602 is applied to the both patients, the scan range does not become a scan range which the operator originally desires to set. Accordingly, as shown in FIG. 7, a map 701 of margin values corresponding to items related to the patient physique e.g. height and weight is generated. Upon inspection, the map 701 is utilized, to refer to a margin value corresponding to the patient physique and apply the value, and it is possible to make the range setting pattern the scan range which the operator originally desires to set. Further, it may be configured such that a margin value with assumption of standard figure patient is designated at step S104, and based on the designated margin value corresponding to the height and weight of standard figure, the margin value map 701 at step S106 is generated.

Note that the margin value map corresponding to physique difference has described as an example. Another margin value map utilizing other patient information may be generated. Further, an average value of margin values obtained by generating and referring to plural margin value maps may be applied.

(Step S107) Linking to Inspection Protocol

At this step, the range setting pattern generated at steps S101 to S105 is linked to an inspection protocol. The method of linking to an inspection protocol, may be, e.g., setting in inspection protocol unit, or may be further finely setting in scan sequence or multi-recon in reconstruction processing unit. Further, it may be configured such that the linking is set in inspection position unit, and automatic setting is utilized regardless of protocol used in inspection. Note that it is desirable that the linked information is stored in the storage device 123 or the like as in the case of the inspection protocol.

Figure 4:
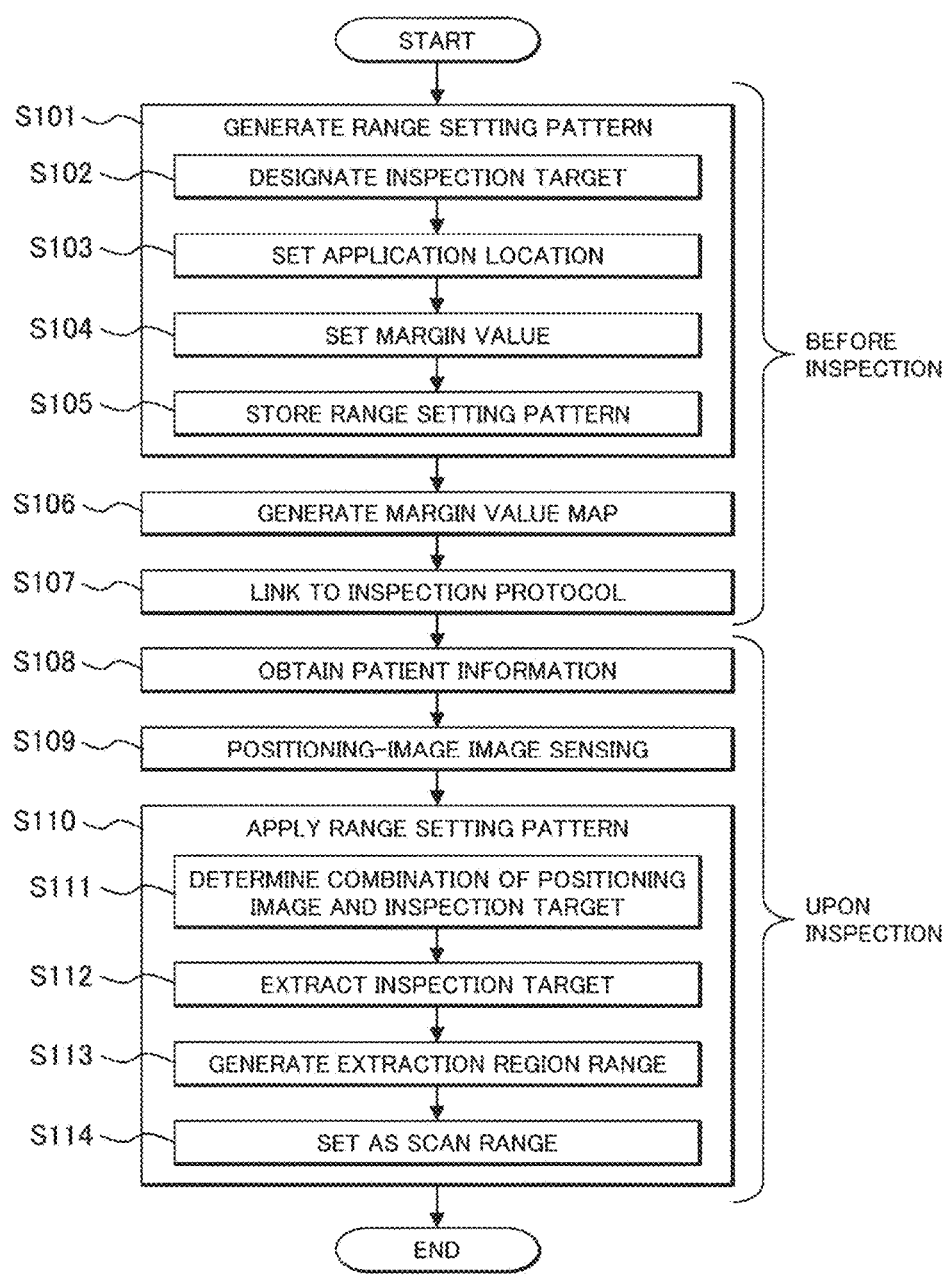
FIG. 4 is a diagram showing a processing flow for scan range setting according to Example 1.

As described above, the pre-inspection part of the processing flow for scan range setting by range setting pattern generation in FIG. 4 is completed. Thereafter, the processing during inspection (S108 to S114) is started.

(Step S108) Acquisition of Patient Information

At this step, the patient information is obtained at the start of inspection. Generally, various information of the patient is inputted at the start of inspection, then patient registration is performed, and stored in the storage device 123. The patient information obtained here is e.g. height, weight and the like.

(Step S109) Image Sensing of Positioning Image

The operator performs setting of the patient on the table, then sets an X-ray irradiation range including a position to be inspected, and performs image sensing of a positioning image. Regarding the positioning image, it is desirable to perform image sensing from at least one direction, e.g., from one of the position of the X-ray tube 101 in FIG. 1 (0°: PA direction) and the position rotated at 90° (LAT direction).

(Step S110) Application of Range Setting Pattern

In the apparatus configuration of the present example, after the image sensing of the positioning image, the operator does not especially perform any operation. In accordance with the range setting pattern linked to the inspection protocol at step S107, the above-described scan range automatic setting unit applies the range setting pattern, thus performs scan range automatic setting.

Hereinbelow, S111 to S114 as steps of range setting pattern application will be described.

(Step S111) Determination of Combination Between Positioning Image and Inspection Target At this step, the number of times of extraction of the designated inspection target (hereinbelow, extraction processing) is determined by applying an extraction algorithm to the positioning image image-sensed at S109. The processing time of the extraction processing is larger in comparison with processing time of inspection information transmission/reception or the like. Particularly, the processing time of the extraction processing is further larger when plural range setting patterns linked to one inspection protocol are set. Accordingly, to minimize the processing time of the extraction processing, the combination between the positioning image and the inspection target is determined so as to minimize the number of processing times.

Figure 8:
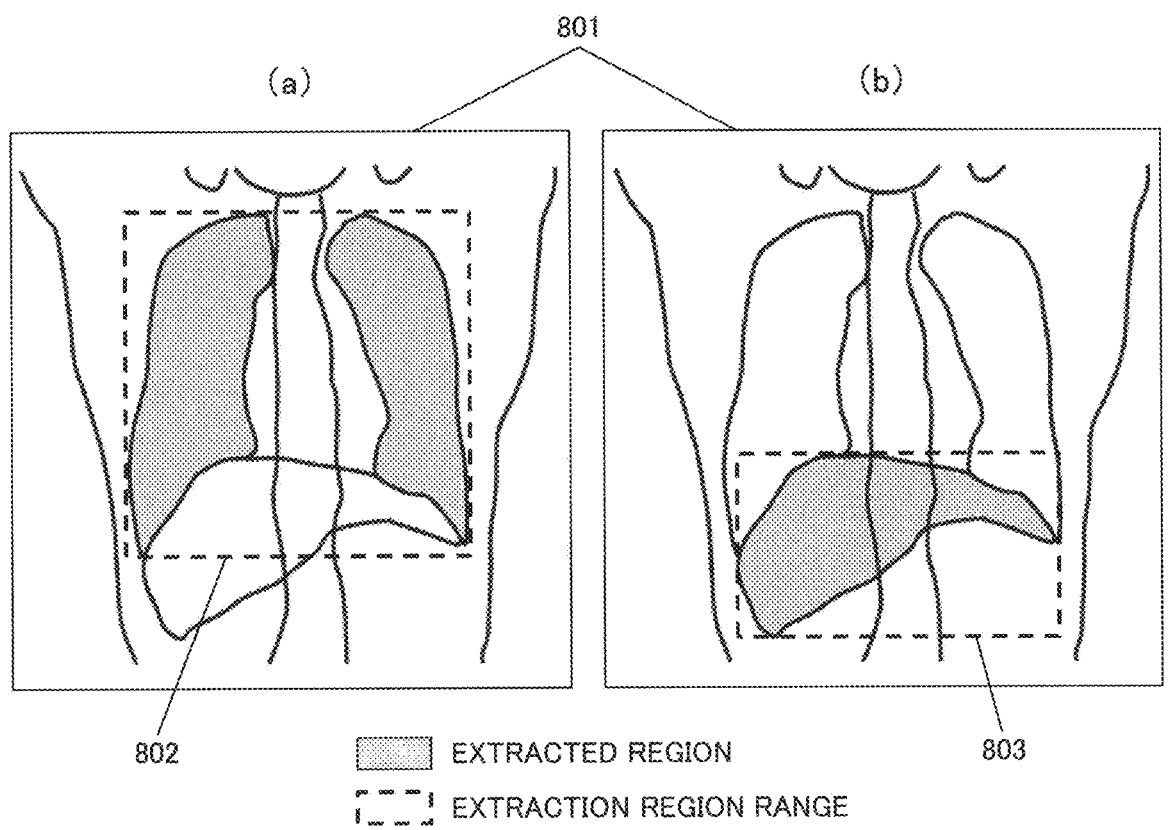
FIG. 8 is a diagram for explaining generation of an extraction region range according to Example 1.

For example, a case where a range setting pattern A (inspection target: lung field, margin values: all 20) and a range setting pattern B (inspection target: lung field, margin values: all 30), further, a range setting pattern C (inspection target: liver, margin values: all 20) are set with respect to one inspection protocol, and only one positioning image 801 as shown in FIG. 8 is image-sensed, will be described. In FIGS. 8(*a*) and (*b*), extracted regions shown in gray respectively indicate the lung field and the liver of the inspection target. In the range setting pattern A and the range setting pattern B, as the inspection target is the same, i.e., the lung field, accordingly, an extraction region range 802 as a result of extraction processing with respect to the same positioning image 801 is the same. Accordingly, after the execution of the extraction processing on the lung field, the respective margin values 20 and 30 are added to the extraction region range 802, and set as a scan range of the range setting pattern A and the range setting pattern B. Similarly, after the execution of the extraction processing on the liver, the range setting pattern C where the margin value 20 is added to an extraction region range 803 is set as a scan range.

Accordingly, the extraction processing with respect to the positioning image 801 in this case may be performed only twice.

(Step S112) Extraction of Inspection Target

At this step, the designated inspection target is extracted from the positioning image 801. The target is extracted by applying an arbitrary extraction algorithm to the positioning image 801. The method of inspection target extraction and the extraction algorithm may be publicly-known methods. For example, the methods as described in PTL 1 may be used.

(Step S113) Generation of Extraction Region Range

At this step, a rectangular extraction region range including the region extracted at S112 is generated. For example, as in the case of the lung field shown in FIG. 8(*a*) and the liver shown in the figure (b), it is possible to generate the extraction region ranges 802 and 803 with the minimum rectangular range including the respective extracted regions shown in gray.

(Step S114) Setting as Scan Range

At this step, the margin values 20, 20, and 30 designated at S104 are respectively added to the positions of the extraction region ranges 802 and 803 generated at S113, then range parameters are calculated, and set as scan ranges of the image sensing conditions.

According to the configuration of the present example as described in detail, by utilizing the range setting pattern having the extraction region range and the margin values, it is possible to, in infallibly correspondence with scan range setting reference which differs by hospital or operator, automatically set a scan range which the operator desires with high accuracy. Further, since the scan range is automatically set with the scan range automatic setting unit in accordance with at least one range setting pattern, linked to an inspection protocol immediately after image sensing of a positioning image, it is possible to greatly improve the operator's labor and inaccuracy upon scan range setting.

Example 2

Figure 9:
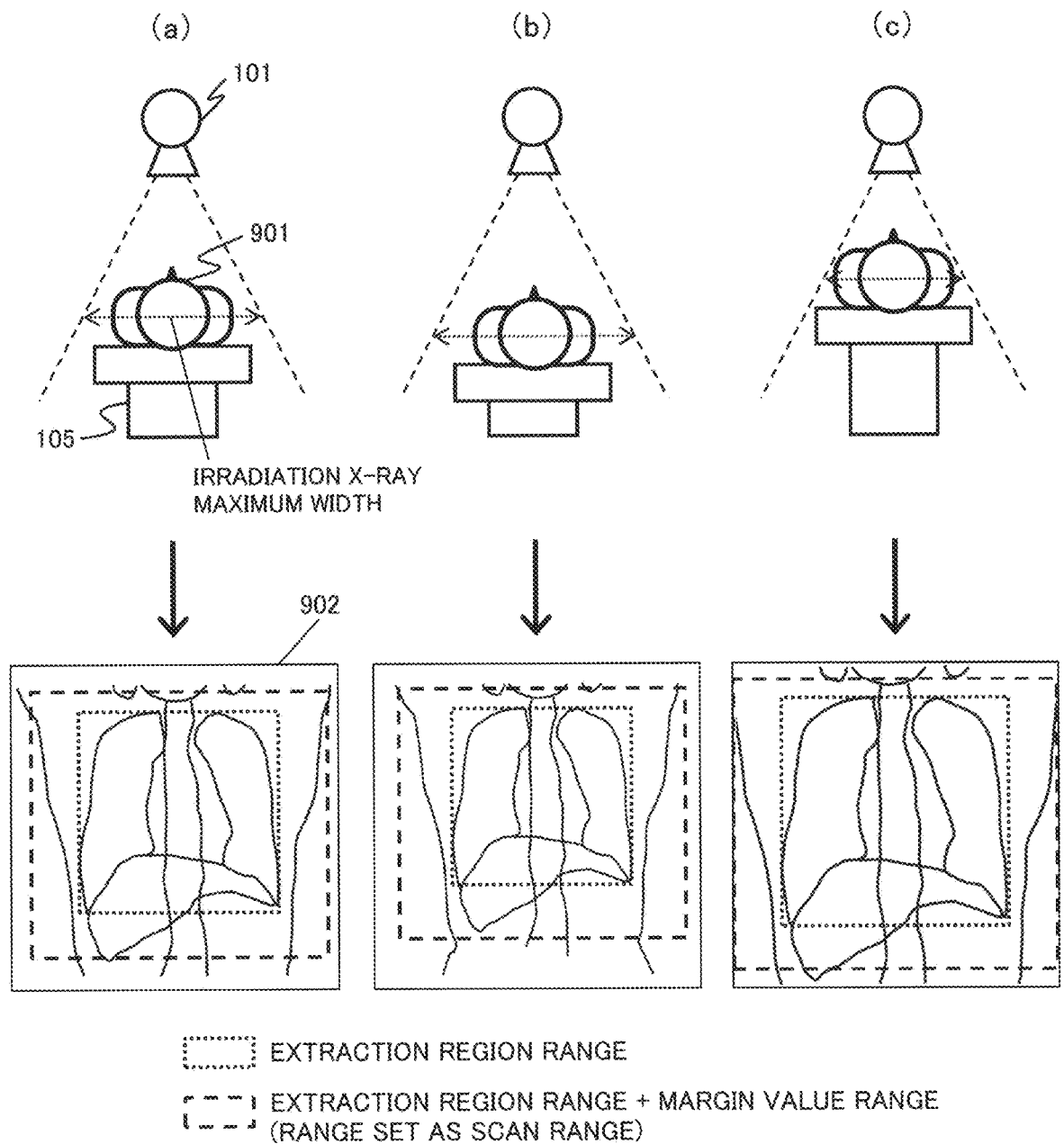
FIG. 9 is a diagram for explaining the difference in irradiation X-ray maximum width by table height according to Example 2.

Next, Example 2 will be described by using FIG. 9 to FIG. 11. In Example 2, in addition to automatic scan range setting as in the case of Example 1, an example in consideration of the influence of the height of the table on which the patient is set, will be described. That is, it is an example configured such that a map in which heights of the table on which the patient is placed and image magnification of positioning image are made to correspond to each other is stored in the storage part, and the scan range automatic setting unit refers to the map, and in correspondence with table height upon inspection, adjusts the margin values stored in the range setting pattern, to set the scan range.

Upon instruction, the table on which the patient is placed is moved mainly in the body axis direction and a body width direction, to be set in a position where the image sensing target can be image-sensed. In some cases, the table height is adjusted. As shown in FIGS. 9(*a*), (*b*) and (*c*), as the maximum width of the X-ray irradiated to a patient 901 differs in accordance with height of the table 105, the magnification of the patient 901 within a positioning image 902 (hereinbelow, image magnification) differs. When the X-ray tube 101 is on the upper side of the table, the image magnification is lower as the table 105 is lower as shown in the figure (b), while as the table is higher as shown in the figure (c), the image magnification is higher. Accordingly, the margin values intended by the operator are not obtained in accordance with height of the table 105. Accordingly, it is necessary to adjust the margin values in correspondence with height of the table 105.

That is, the difference in Example 2 from Example 1 is that a map in which heights of the table on which the patient is placed and image magnifications of positioning image are made to correspond to each other, as shown in FIG. 10, is previously generated, and the set margin values are adjusted in correspondence with table height upon inspection, and set as a scan range.

Figure 11:
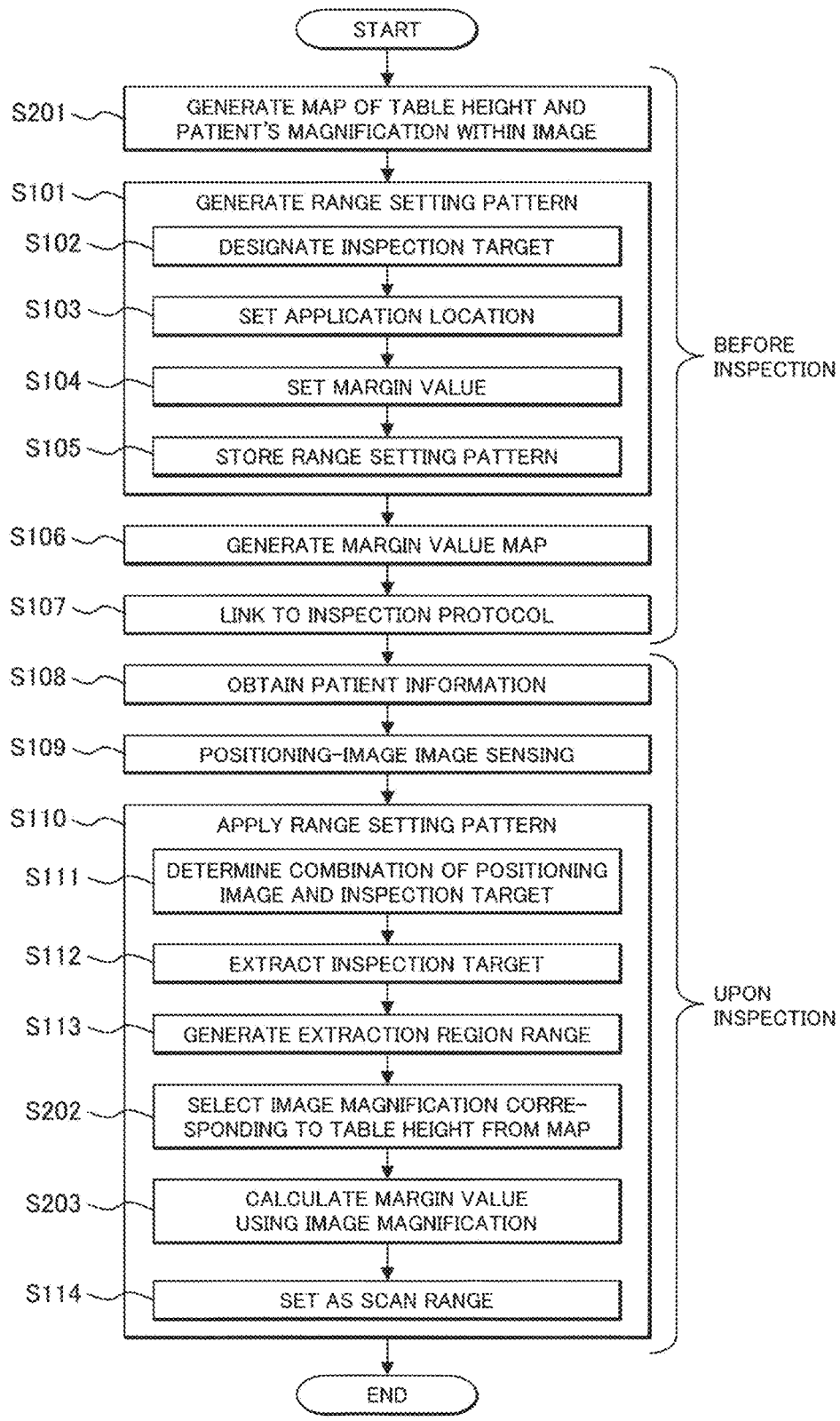
FIG. 11 is a diagram showing the processing flow for scan range setting according to Example 2.

FIG. 11 is a processing flowchart for scan range setting according to Example 2. Steps S101 to S114 in FIG. 11 are the same as those in Example 1. Hereinbelow, only parts different from the processing flow in Example 1 will be described, and explanations of the same parts will be omitted.

(Step S201) Generation of Map of Table Height to Patient Magnification within Image At this step, a map in which the table heights and image magnifications are made to correspond to each other is generated before inspection.

As described above, as the maximum width of the X-ray irradiated to the patient differs in accordance with table height, the image magnification is lower when the table is lower, while higher when the table is higher. For example, FIG. 10 shows an example of the map in which the table heights and the image magnifications are made to correspond to each other when the table height is 200 mm and the magnification is 1.0. A map 1001 in the figure (a) corresponds to a case where the X-ray tube 101 is on the upper side of the table. A map 1002 in the figure (b) corresponds to a case where the X-ray tube 101 is on the lower side of the table. As shown in the figures, when the X-ray tube 101 is on the upper side of the table 105, the image magnification is higher as the table height is higher. When the X-ray tube 101 is on the lower side of the table 105, the image magnification is reduced.

(Step S202) Selection of Image Magnification Corresponding to Table Height from Map At this step, the height of the table 105 upon image sensing of a positioning image is obtained at step S109, then the image magnification corresponding to the obtained table height is selected from the map generated at step S201.

(Step S203) Calculation of Margin Value Using Image Magnification

At this step, in accordance with the image magnification selected at step S202, the margin value set in the range setting pattern is adjusted. For example, in an inspection protocol where the range setting pattern A (margin values: all 20) is set, the map 1001 in FIG. 10(a) is used. When the table height upon image sensing of the positioning image is 190 mm, the margin value is adjusted to 18. Thereafter, the processing flow the same as that in Example 1 is performed.

According to the present example, as a scan range desired by the operator is automatically set regardless of table height upon image sensing, the inaccuracy in scan range setting is further improved.

Example 3

Figure 12:
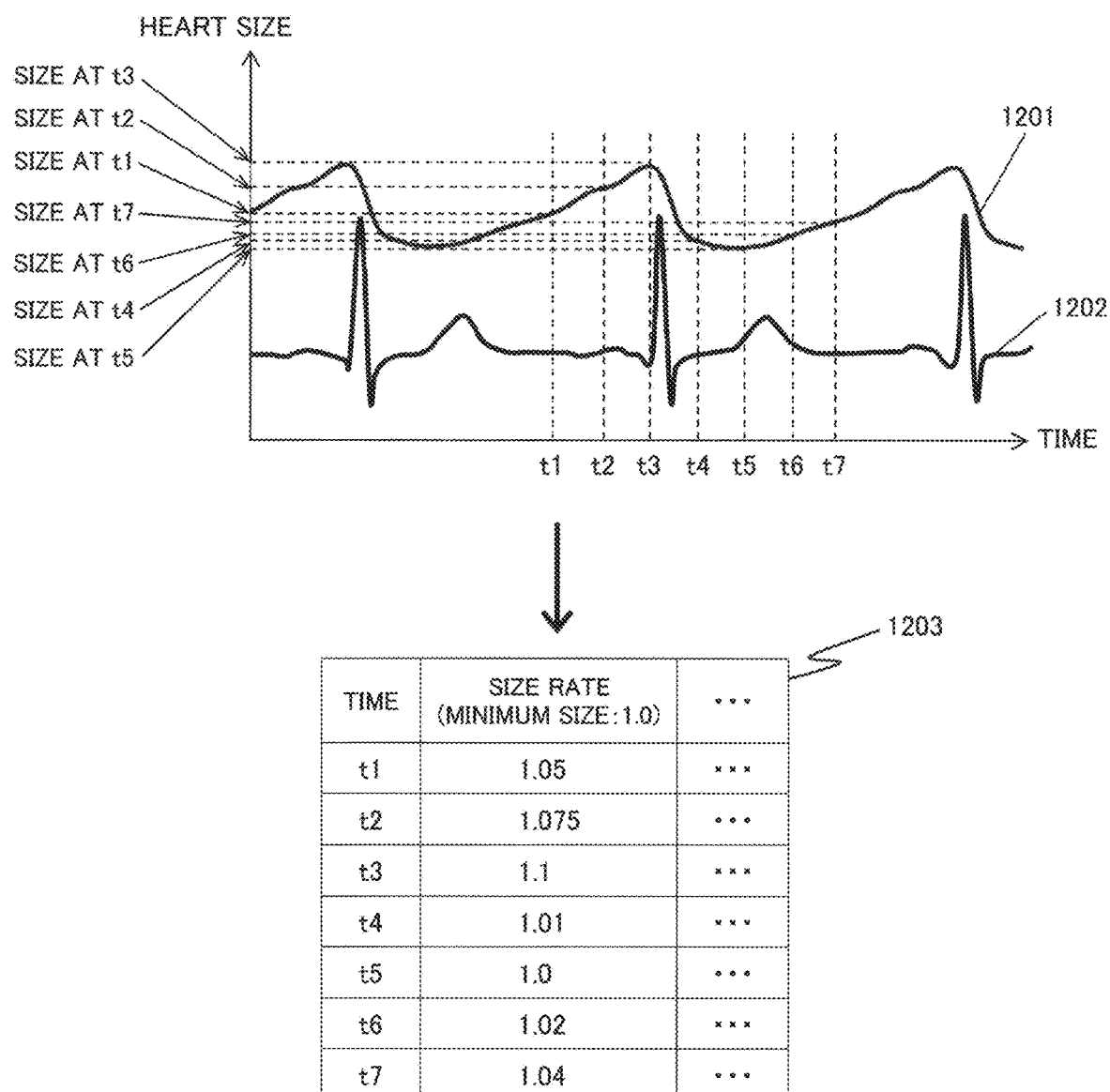
FIG. 12 is a diagram showing an example where an electrocardiographic waveform and a heart size are made to correspond to each other, according to Example 3.

Next, Example 3 will be described by using FIG. 12 and FIG. 13. The present example is an example configured such that a map in which electrocardiographic waveforms of the patient and movements of the heart are made to correspond to each other is stored in the storage part, and the scan range automatic setting unit refers to the map based on the electrocardiographic waveform of the patient obtained upon image sensing of the positioning image, adjusts the margin value stored in the range setting pattern, and sets the scan range.

Among the body parts to be inspection targets include a part which always moves and a part which almost does not move, or does not move at all. When the inspection target is an organ which always moves, the position and the size of the organ may differ from those upon positioning-image image sensing. When the inspection target moves out of the set scan range during actual image sensing, an image necessary for diagnosis is not obtained. Accordingly, it is necessary to set the scan range so as to include the inspection target even when the position and the size of the organ is different.

Accordingly, in Example 3, when an organ which moves is the inspection target, the fluctuating position and the displacement of size of the organ are estimated, and the influence of them are added in calculation of the margin value. For example, when the inspection target is a heart, electrocardiogram synchronized image sensing is generally used. The electrocardiogram synchronized image sensing method includes a method of obtaining an electrocardiogram of the patient and irradiating an X-ray only in a desired cardiac phase while referring to the electrocardiogram (hereinbelow, prospective scanning) and a method of performing helical image sensing to simultaneously obtain an electrocardiographic waveform and projection data of the patient (hereinbelow, retrospective scanning). In the case of the prospective scanning, as image sensing timing is designated with respect to the electrocardiogram, the margin values are adjusted in correspondence with position and size at the designated timing. In the case of the retrospective scanning, the possible fluctuating position and the maximum size during image sensing are estimated, and the margin value is adjusted. For this purpose, association between electrocardiographic waveforms and positions and sizes of the heart is previously performed.

That is, the difference in Example 3 from the above embodiments is that a map in which electrocardiographic waveforms and movements of the heart (fluctuating position and displacement of size) are made to correspond to each other is previously generated, then an electrocardiographic waveform of the patient is obtained at the same time of positioning-image image sensing, then the map is referred to, and the margin value is adjusted such that the san range includes the inspection target, thus set as the scan range.

Figure 13:
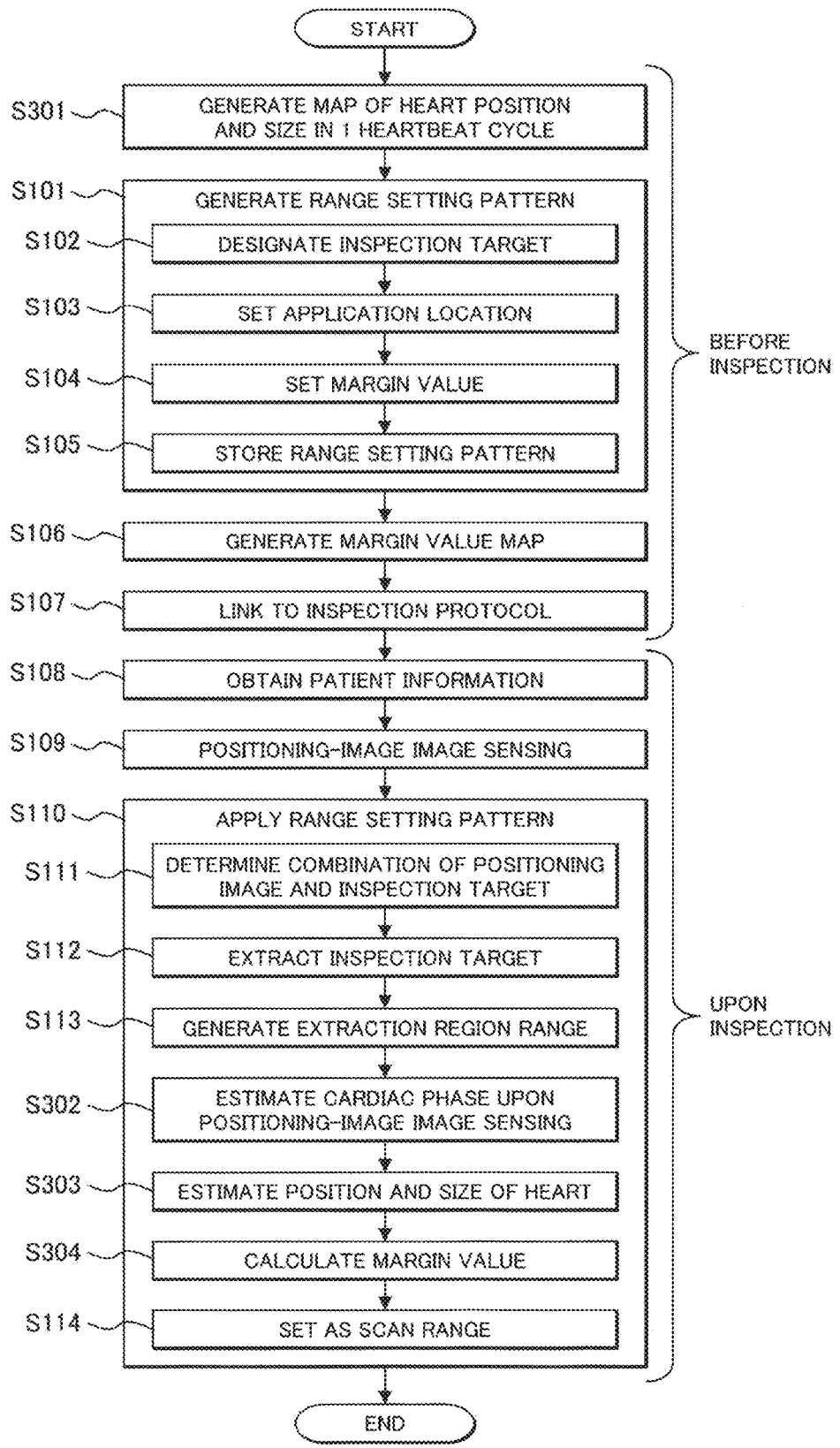
FIG. 13 is a diagram showing the processing flow for scan range setting according to Example 3.

FIG. 13 is a processing flowchart for scan range setting according to Example 3. Here as an example of Example 3, a case where the inspection target is a heart, and the image sensing method is retrospective scanning will be described. Steps S101 to S114 in FIG. 13 are the same as those in the above embodiments. Hereinbelow, only parts different from the above embodiments will be described, and explanations of the same parts will be omitted.

(Step S301) Generation of Map of Position and Size of Heart in 1 Heartbeat Cycle At this step, based on a general electrocardiographic waveform, a map in which positions and sizes of heart are made to correspond to respective cardiac phases in one heartbeat cycle is generated before inspection. For example, FIG. 12 is an example where an electrocardiographic waveform 1202 and a heart size 1201 are made to correspond to each other. The cardiac phases for one heartbeat cycle are divided into time t1 to t7, and a map 1203 of rates with respect to the size when the heart size 1201 is minimum (here at time t5) is generated.

(Step S109) Image Sensing of Positioning Image

In the present example, upon acquisition of positioning image, electrocardiac information such as a cardiac phase is obtained.

(Step S302) Estimation of Cardiac Phase Upon Positioning-Image Image Sensing

At this step, based on the electrocardiac information obtained at step S109, the cardiac phase upon positioning-image image sensing (the position within one heartbeat cycle) is estimated.

(Step S303) Estimation of Position and Size of Heart

At this step, based on the cardiac phase estimated at step S302, the possible fluctuating position and maximum size of the heart during image sensing are estimated. For example, regarding the heart size, by using the map as shown in FIG. 12, based on the size in the cardiac phase upon positioning-image image sensing, the size in the cardiac phase at t3 where the size is maximum is obtained. For example, when the cardiac phase upon positioning-image image sensing is t4 in FIG. 12 and the heart size on the positioning image is 130 mm, the possible maximum heart size upon image sensing is about 141.5 mm.

(Step S304) Calculation of Margin Value

At this step, the margin value is calculated such that, even when the position and size of the heart upon image sensing are the fluctuating position and the maximum size of the heart estimated at step S303, the margin values set in the range setting pattern is maintained. That is, only the difference between the extraction region range with respect to the positioning image and the range in the case of the fluctuating position and the maximum size of the heart estimated at step S303 is added to the margin value set in the range setting pattern. For example, when the margin value in the range setting pattern is 20, the extraction region range with respect to the positioning image is 130, and the maximum size is 140, the scan range is set to 160. That is, the margin value is adjusted to 30.

Here the case where the inspection target is a heart has been described; however, the same method is applicable to other inspection targets. For example, when the inspection target is a lung field/diaphragm, the position and size vary in accordance with respiratory timing. In many cases, the positioning-image image sensing and actual image sensing are performed in a breath-hold state, and the position and the size of the inspection target correspond in both image sensing. However, when breath holding is difficult for the patient, the position and the size of the inspection target do not always correspond in both image sensing. Accordingly, association is performed between respiratory waveform or the like and position/size of the lung field/diaphragm to generate a map, the possible position and size of the organ are estimated from the respiratory timing upon positioning-image image sensing, and the margin value is adjusted.

According to the present example, even when the part of the inspection target is an organ which always moves or the like, it is possible to set a scan range which is desired by the operator and with which an image necessary for diagnosis is obtained. Accordingly, the inaccuracy in scan range setting is further improved.

Example 4

Next, Example 4 will be described by using FIG. 14 to FIG. 17. The present example is an example configured such that the scan range automatic setting unit calculates an inclination θ of the patient with respect to a scan center line from the positioning image, generates an image obtained by rotating the positioning image at θ (hereinbelow, θ-rotated image), then generates an extraction region range with respect to the θ-rotated image, calculates a scan range with respect to the θ-rotated image (hereinbelow, θ-rotated scan range), and sets a value obtained by −θ rotating the θ-rotated scan range as a scan range.

Figure 14:
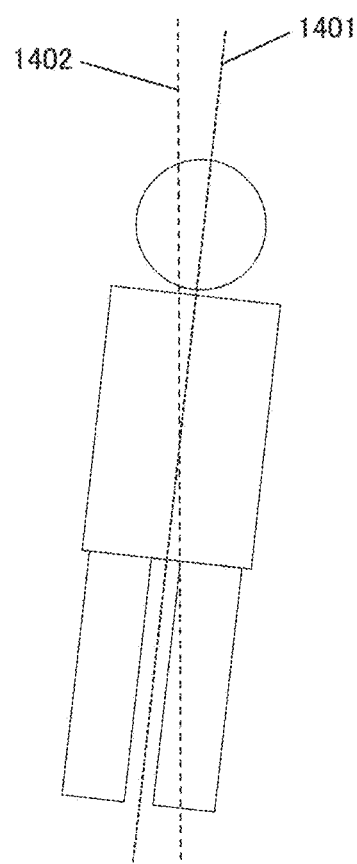
FIG. 14 is a diagram for explaining a case where the patient's body axis is inclined with respect to a scan center line, according to Example 4.

That is, in the present example, in addition to the contents of the above examples, a configuration where, even when the patient cannot lie down straight on the table, i.e., as shown in FIG. 14, a body axis 1401 of the patient is inclined with respect to a scan center line 1402, it is possible to automatically set a scan range, will be described.

Figure 15:
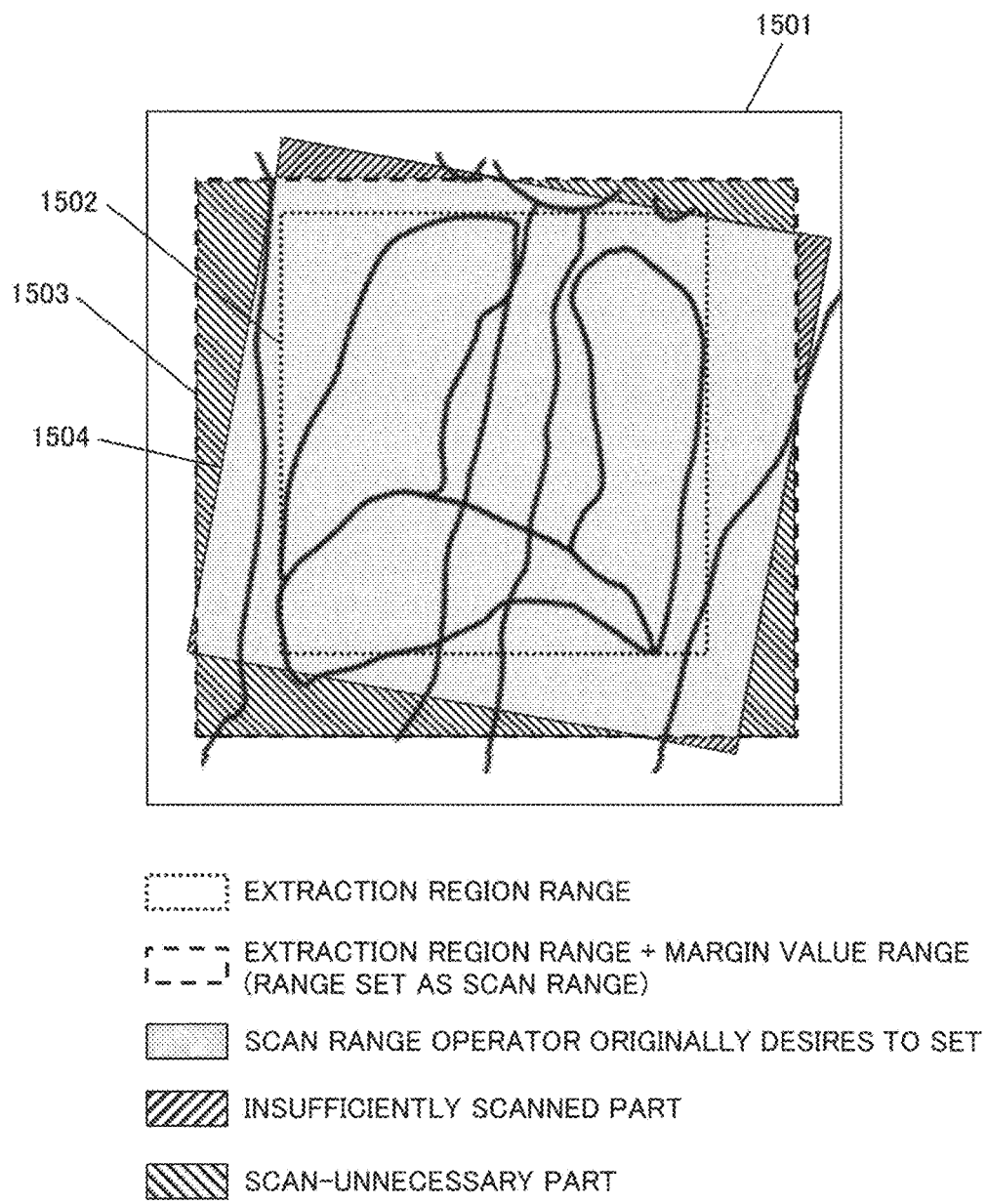
FIG. 15 is a diagram for explaining a scan range where the patient's body axis is inclined, according to Example 4.

When the body axis 1401 of the patient is inclined with respect to the scan center line 1402, the patient appears diagonally on the positioning image. Accordingly, as shown in FIG. 15, an extraction region range 1502 with respect to a positioning image 1501 and a range 1503 of the extraction region range and the margin value are not a scan range 1504 which the operator originally desires to set, and an insufficiently scanned part and a scan-unnecessary part occur. Accordingly, it is necessary to set the extraction region range and the scan range in accordance with degree of inclination of the patient. Accordingly, the degree of inclination of the patient is obtained from the positioning image, then the extraction region range and the scan range when the patient is not inclined are obtained, and the obtained scan range is inclined by the inclination of the patient and set as the scan range.

Figure 16A:
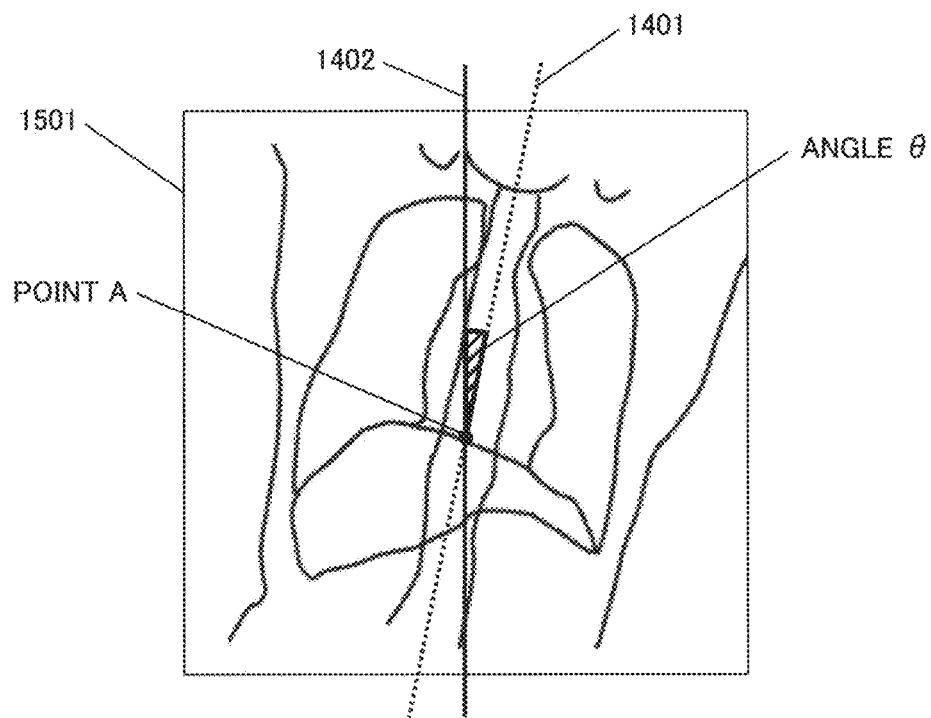
FIG. 16A is a diagram for explaining a scan range calculation method when the patient's body axis is inclined, according to Example 4.
Figure 16B:
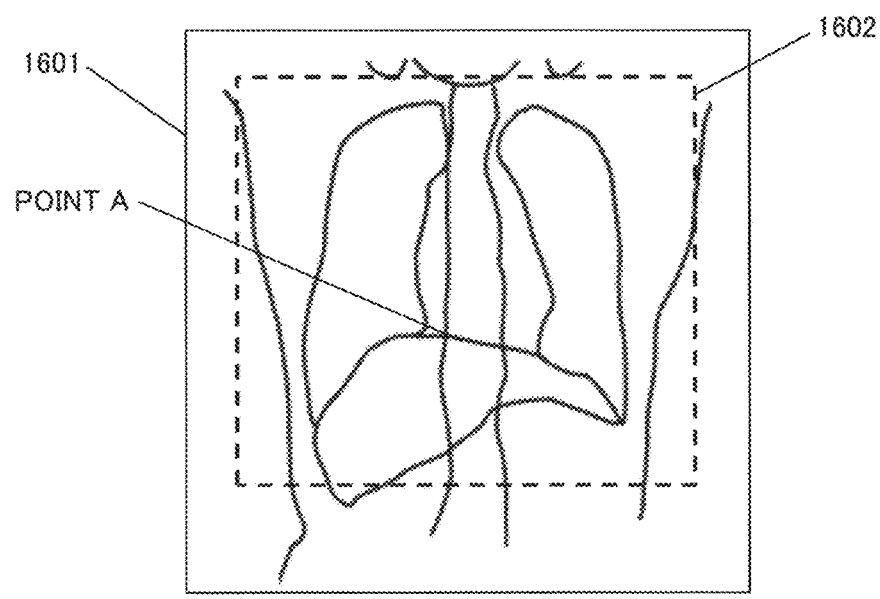
FIG. 16B is a next diagram for explaining the scan range calculation method when the patient's body axis is inclined, according to Example 4.
Figure 16C:
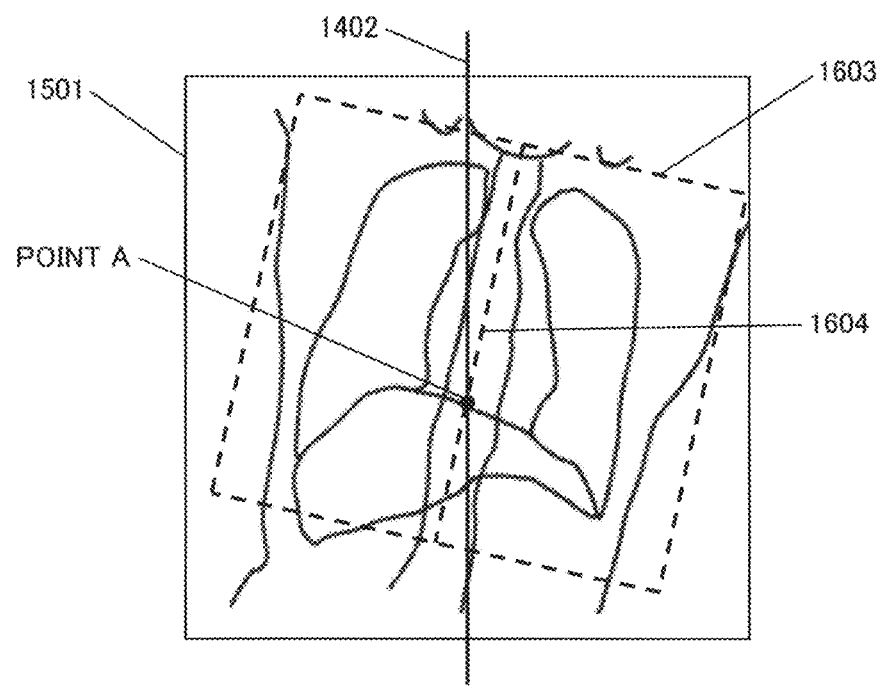
FIG. 16C is a continued diagram for explaining the scan range calculation method when the patient's body axis is inclined, according to Example 4.

That is, the difference from the above-described examples is that as shown in FIG. 16A, an angle θ of the inclination of the body axis 1401 of the patient (the counterclockwise direction is positive) with respect to the scan center line 1402 is calculated from the positioning image 1501, then as shown in FIG. 16B, a θ-rotated image 1601 obtained by θ-rotating the positioning image 1501 is generated, then an extraction region range is generated with respect to the θ-rotated image 1601, a θ-rotated scan range 1602 as a scan range with respect to the θ-rotated image is calculated, and as shown in FIG. 16C, a value obtained by −θ rotating the θ-rotated scan range 1602 is set as a scan range 1603. Note that in FIG. 16C, numeral 1604 denotes a center line of the scan range 1603.

Figure 17:
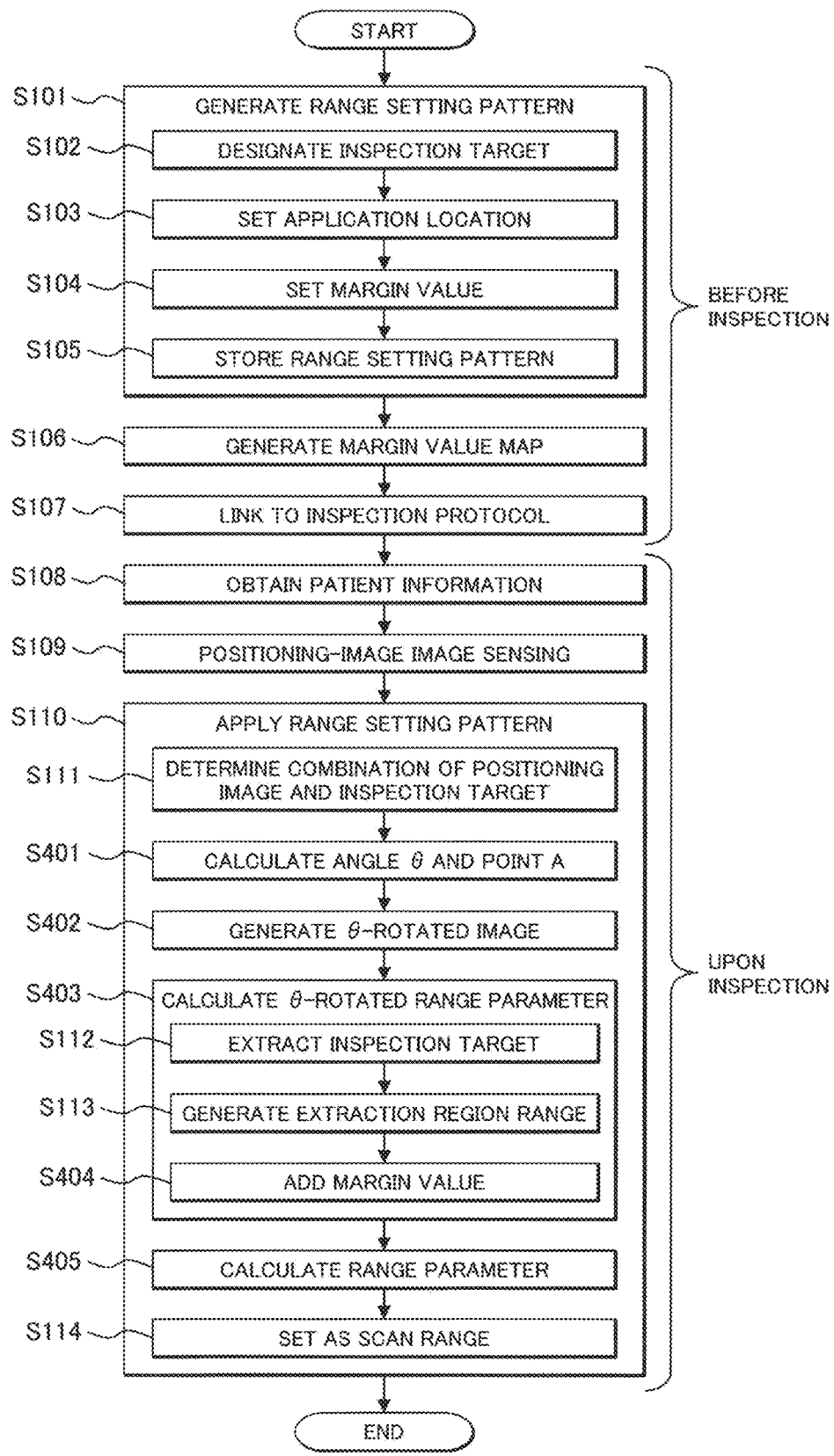
FIG. 17 is a diagram showing the processing flow for scan range setting according to Example 4.

FIG. 17 is a processing flowchart for scan range setting according to Example 4. Steps S101 to S114 in FIG. 17 are the same as those in the above examples. Hereinbelow, only parts different from the above embodiments will be described, and explanations of the same parts will be omitted.

(Step S401) Calculation of Angle θ and Point A

At this step, as shown in FIG. 16A, the body axis 1401 of the patient is obtained based on the positioning image 1501, and an angle θ formed with the scan center line 1402 and the body axis 1401 of the patient, and an intersection A between the scan center line and the body axis of the patient are obtained. The method of obtaining the body axis 1401 of the patient may be, e.g. obtaining the body axis by interpreting a CT value of the positioning image, or by mounting a sensor or CCD camera in the table or the scan gantry part, separately obtaining and analyzing the setting state of the patient, or by other publicly-known methods.

(Step S402) Generation of θ-Rotated Image

At this step, a θ-rotated image 1601 obtained by θ-rotating the positioning image obtained at step S109, as shown in FIG. 16B, is generated. The θ-rotated image 1601 is an image corresponding to a positioning image image-sensed when the scanning center and the body axis of the patient are not inclined. The method of rotation is, e.g., a method utilizing a rotation matrix represented with the following expression is known. The following expression 1 is for calculating a point C (cx, cy) obtained by rotating a point B (bx, by) at the angle θ around a point A (ax, ay).

[Expression 1]

$$\begin{pmatrix} cx \\ cy \end{pmatrix} = \begin{pmatrix} \cos\theta & -\sin\theta \\ \sin\theta & \cos\theta \end{pmatrix} \begin{pmatrix} bx - ax \\ by - ax \end{pmatrix} + \begin{pmatrix} ax \\ ay \end{pmatrix} \qquad (1)$$

Note that the method of rotation may be other publicly-known methods than the abovementioned expression 1.

(Step S403 and S404) Calculation of θ-Rotated Range Parameter

At this step, a θ-rotated range parameter is calculated from the θ-rotated image generated at step S402. Steps S112 and S113 are the same processing as that in the above embodiments. At step S404, the margin value set in the range setting pattern is added to the extraction region range with respect to the θ-rotated image, and a range parameter is calculated as the θ-rotated range parameter.

(Step S405) Calculation of Range Parameter

At this step, a range parameter is calculated by −θ rotating the θ-rotated range parameter calculated at step S404, as shown in FIG. 16C. The method of rotation may be the method described as above, or may be other publicly-known methods.

(Step S114) Setting as Scan Range

Further, a center line 1604 of the scan range 1603 calculated as in the case of the above-described step is inclined with respect to the scan center line 1402 as shown in FIG. 16C. To set this scan range 1603, it may be configured such that e.g., in the case of an X-ray irradiation range, a collimator capable of forming a fine irradiation shape as suggested in Japanese Patent Application Laid-Open No. 2015-59889 is used as the collimator 103, and scanning is performed following the scan range 1603 shown in FIG. 16C. In the case of an image generation range, it is not necessary to add any particular mechanical composition.

According to the present example, even when the body axis of the patient is inclined with respect to the scanning center, it is possible to set a scan range to perform scanning desired by the operator and attain a minimum exposure dose without excess or deficiency of data acquisition.

Example 5

Figure 18:
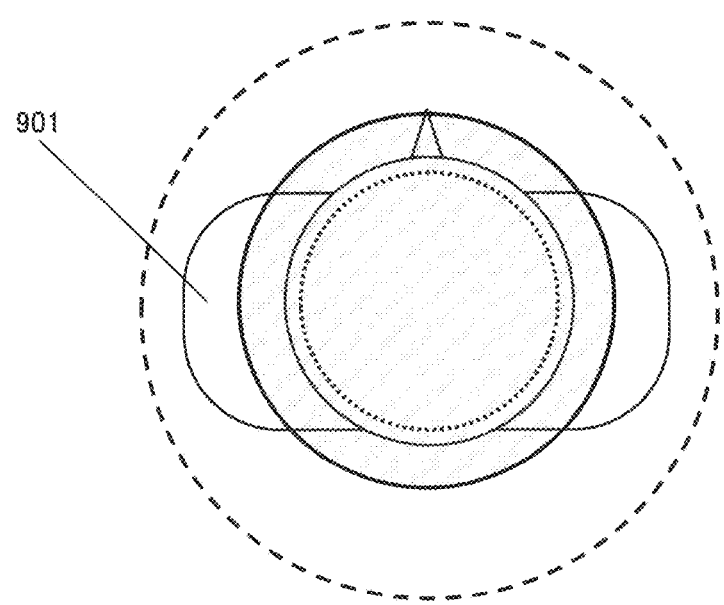
FIG. 18 is a diagram for explaining a collection FOV and a patient size, according to Example 5.

Next, Example 5 will be described by using FIG. 18 to FIG. 20. The present example is an example configured such that a map, in which the FOV of an extraction region range with respect to the positioning image (hereinbelow, extraction FOV) and an FOV upon image sensing to attain appropriate BH correction degree to reduce the influence on an image by beam hardening (hereinbelow, BH) are made to correspond to each other, is stored, and the scan range automatic setting unit refers to the map, and sets a collection FOV corresponding to the extraction FOV as a scan range. That is, in the present example, in addition to the contents of the above-described examples, an example where the collection FOV is set so as to attain appropriate BH correction to reduce the influence on an image by BH in the X-ray CT apparatus will be described.

In the BH correction, the CT value is corrected assuming that the patient has a size equal to the collection FOV. Accordingly, as shown in FIG. 18, when the collection FOV set with respect to the size of a patient 901 is not appropriate, the BH correction is not appropriate, and cupping or capping of the CT value occurs, which adversely affects the image.

Figure 19:
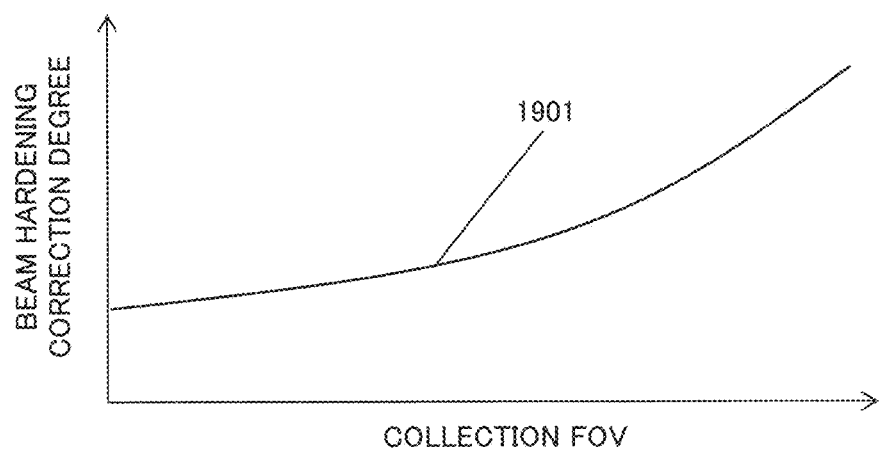
FIG. 19 is a diagram for explaining the relationship between the collection FOV and beam hardening correction according to Example 5.

Accordingly, by utilizing a BH correction degree 1901 which is determined by collection FOV as shown in FIG. 19, in correspondence with the extraction FOV, the value of the collection FOV so as to attain an appropriate BH correction degree is set as a scan range. That is, the difference from the above examples is that a map in which an extraction FOV with respect to the positioning image and a collection FOV to attain an appropriate BH correction degree are made to correspond to each other is previously generated, and a collection FOV corresponding to the extraction FOV is set as a scan range.

Figure 20:
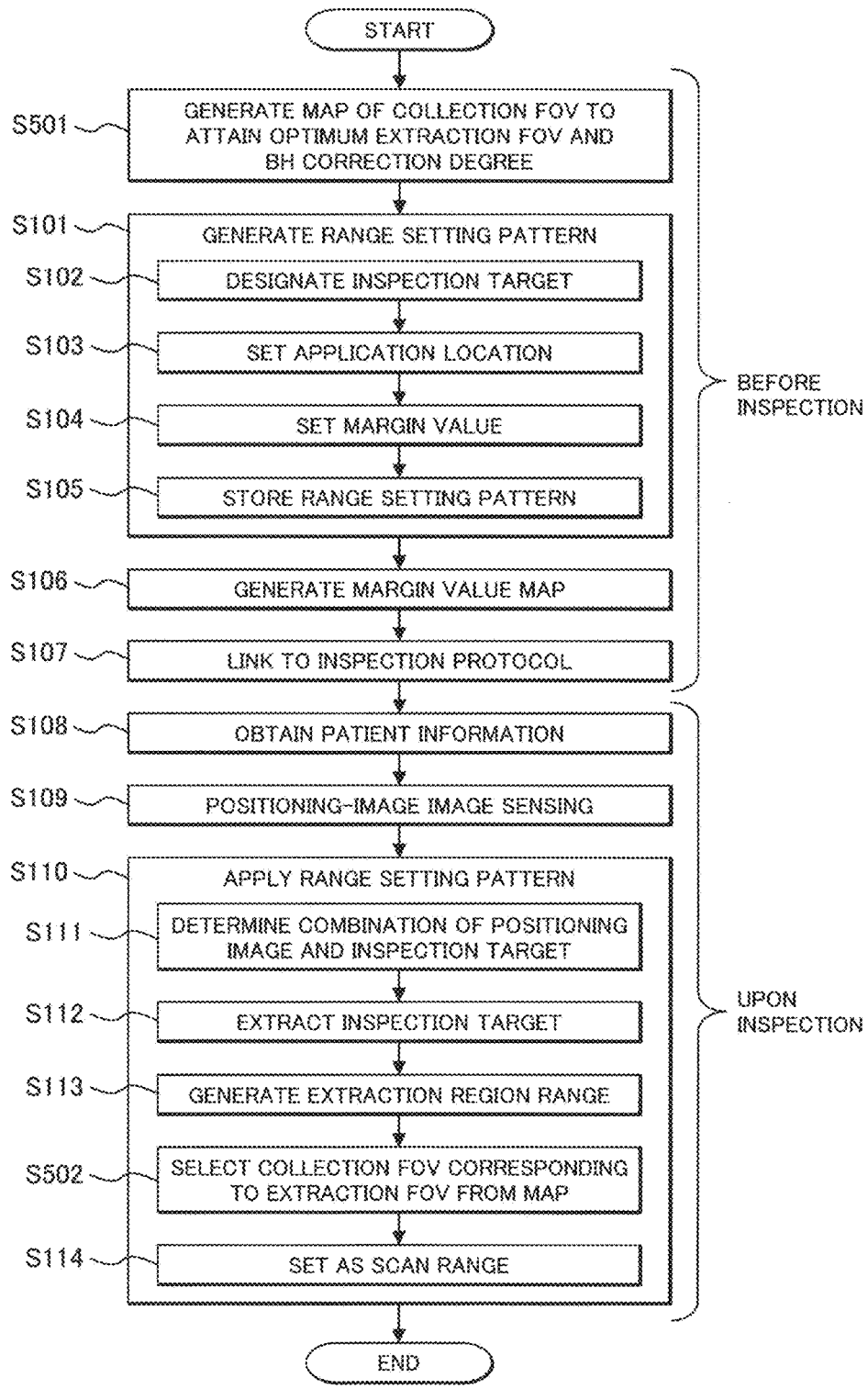
FIG. 20 is a diagram showing the processing flow for scan range setting according to Example 5.

FIG. 20 is a processing flowchart for scan range setting in Example 5. Steps S101 to S114 in FIG. 20 are the same as those in the above examples. Hereinbelow, only parts different from the above embodiments will be described, and explanations of the same parts will be omitted.

(Step S501) Generation of Map of Collection FOV to Attain Appropriate BH Correction Degree and Extraction FOV At this step, as described above, by utilizing the BH correction degree 1901 which is determined by collection FOV as shown in FIG. 19, a map in which extraction FOVs and collection FOV values to attain an appropriate BH correction degree are made to correspond to each other is generated before inspection.

(Step S502) Selection of Collection FOV Corresponding to Extraction FOV from Map At this step, a collection FOV corresponding to an extraction FOV of the extraction region range generated at S113 is selected by using the map generated at step S501. Further, the collection FOV selected here is set as a scan range; however, it may be configured such that, means for selecting e.g., the value of the FOV obtained in the present example, or the value of an FOV calculated by the method in the above examples, to be set as a scan range, is provided.

According to the present example, it is possible to perform appropriate beam hardening correction while infallibly setting the inspection target within the scan range. Accordingly, the inaccuracy in the scan range setting and image quality are improved.

Example 6

Next, Example 6 will be described by using FIG. 21. The present example is an example configured such that when the operator adjusts the scan range, the scan range automatic setting unit accumulates scan range adjustment information as information on the adjustment of the scan range in the storage part, and in next inspection, the scan range automatic setting unit sets a scan range with a margin value optimized based on the accumulated scan range adjustment information. That is, in the present example, even in a case where a scan range is automatically set as in the case of the above examples, since the operator manually adjusts the scan range in some cases, when manual adjustment is performed, the scan range adjustment information is sequentially accumulated. Then the margin value is optimized based on the scan range adjustment information, and a scan range to which the optimized margin value is applied is set in the next and the subsequent inspections.

Figure 21A:
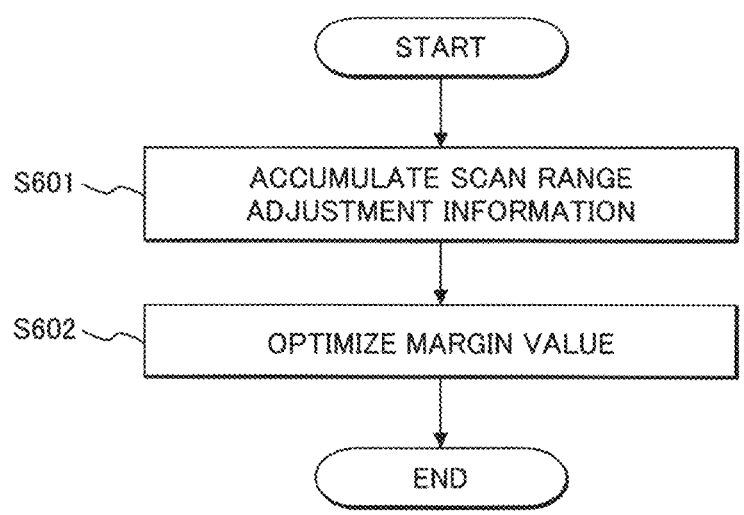
FIG. 21A is a diagram showing a pre-processing flow for the scan range setting according to Example 6.
Figure 21B:
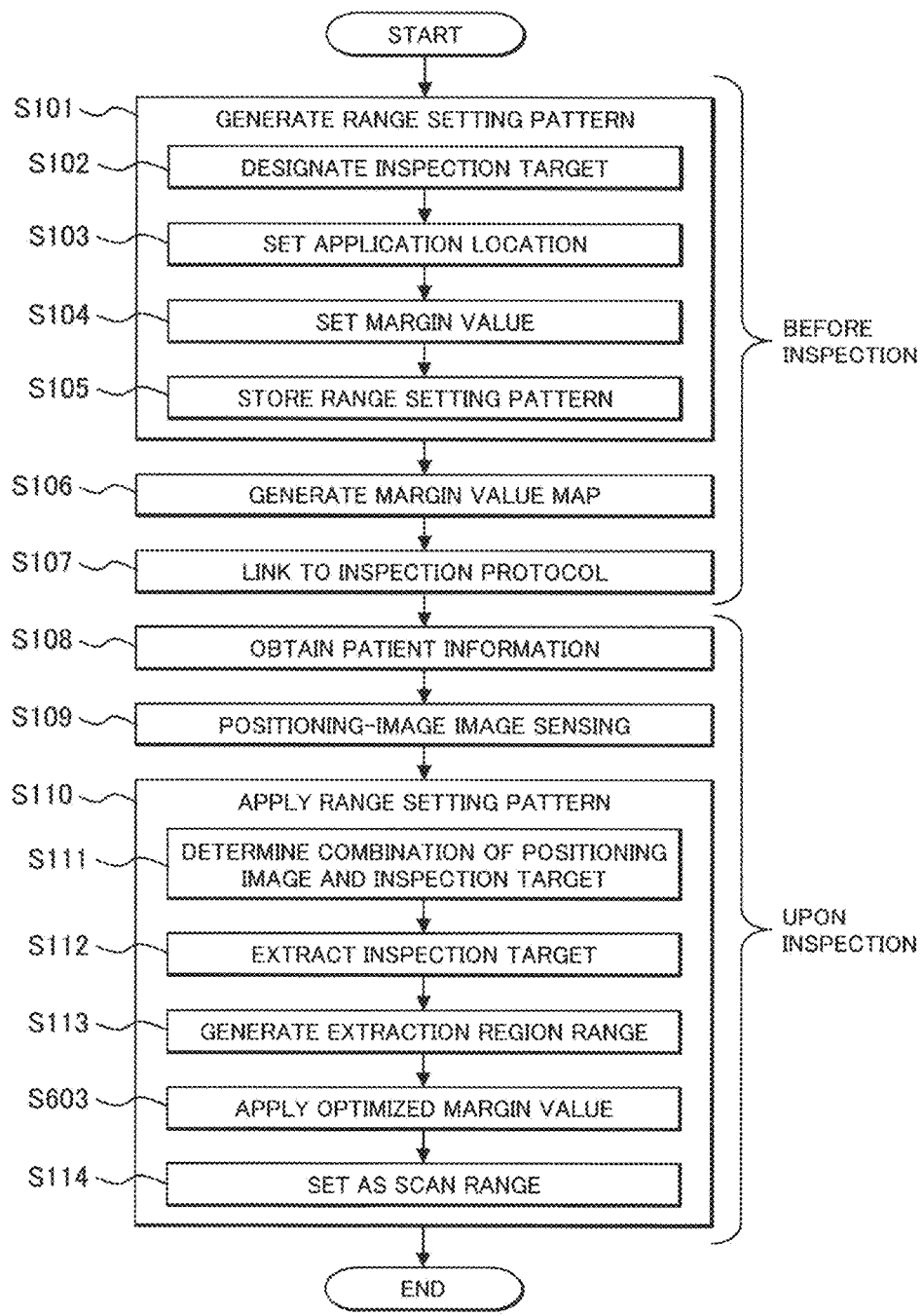
FIG. 21B is the processing flow for scan range setting according to Example 6.

FIGS. 21A and 21B are preprocessing and processing flowcharts for scan range setting according to Example 6. Steps S101 to S114 in FIG. 21B are the same as those in the above examples. Hereinbelow, only parts different from the above embodiments will be described, and explanations of the same parts will be omitted. First, the flowchart of FIG. 21A will be described.

(Step S601) Accumulation of Scan Range Adjustment Information

After the setting of the scan range as described in the above example, the operator manually adjusts the scan range, then actual image sensing is performed, and the scan range adjustment information is accumulated in a storage device or the like. The scan range adjustment information is, e.g., the pattern of the positioning image, the height and the weight of the patient, the part of the inspection target, the electrocardiac information, the position of the extraction region range with respect to the positioning image, the position and adjustment amount manually adjusted with respect to the automatically set scan range, and various image sensing conditions are given, further, other information than these information may be added and accumulated.

(Step S602) Optimization of Margin Value

At this step, based on the scan range adjustment information accumulated at step S601, the margin value of the range setting pattern is optimized. As the method of optimization, a method of utilizing a machine learning program, or other publicly-known methods may be used. Next, the flowchart of FIG. 21B will be described.

(Step S603) Use of Optimized Margin Value

At this step, after the generation of the extraction region range at step S113, the margin value optimized at step S602 is applied. Further, it may be configured such that, means for selecting application of, e.g., the optimized margin value, or the margin value calculated by the method in the above examples, is provided.

According to the present example, it is possible to follow scan range setting reference which differs by hospital or user with high accuracy. Further, the difference in accuracy in scan range setting due to the user's experience and technique is further eliminated.

As described above, various examples of the present invention in an X-ray CT apparatus have been described, and the invention is applicable to other medical image diagnostic devices or medical equipment which obtains a positioning image and which has image-sensing planning operation using the positioning image.

Further, the present invention is not limited to the abovementioned examples, but includes various modifications.

For example, the abovementioned examples have been described in detail for better understanding of the present invention, and the invention is not necessarily limited to an embodiment having all the described constituent elements. Further, constituent elements of an embodiment may be replaced with those of another embodiment, and further, constituent elements of an embodiment may be added to those of another embodiment. Furthermore, it is possible to perform addition/deletion/replacement with respect to some of constituent elements of the respective embodiments with other constituent elements.

Further, regarding the above-described respective constituent elements, the functions, the system controller, the image arithmetic device and the like, mainly an example of generation of a program to realize some or all of them has been described. It goes without saying that some or all of them may be realized with hardware by designing as e.g. an integrated circuit. That is, all or some of functions of the controller may be replaced with a program, and realized with an integrated circuit or the like such as an ASIC (Application Specific Integrated Circuit) or an FPGA (Field Programmable Gate Array).

REFERENCE SIGNS LIST

1: X-ray CT apparatus, 100: scan gantry part, 101: X-ray tube, 102: rotary disc, 103: collimator, 104: opening, 105: table, 106: X-ray detector, 107: data collection device, 108: gantry control device, 109: table control device, 110: X-ray control device, 120: console, 121: input device, 122: image calculation device, 123: storage device, 124: system control device, 125: display device, 201, 503, 601, 801, 902, 1501: positioning image, 202: automatically set scan range, 203, 1504: scan range operator originally desires to set, 301: intersection between clavicle and a rib, 302: cavity of a shoulder formed between a raised arm and a head, 501: range setting pattern generation screen, 502: range setting pattern details setting unit, 504, 802, 803, 1502: extraction region range, 505: range set as scan range upon inspection, 602: margin value, 701, 1001, 1002, 1203: map, 901: patient, 1201: heart size, 1202: electrocardiographic waveform, 1401: body axis of patient, 1402: scan center line, 1503: range of extraction region range and margin value, 1601: θ-rotated image, 1602: θ-rotated scan range, 1603: scan range, 1604: center line of scan range, 1901: beam hardening (BH) correction degree

The invention claimed is:

1. A medical image diagnostic device comprising:
a storage part that links a range setting pattern in which an inspection target and a margin value are made to correspond to each other, to an inspection protocol, and stores the range setting pattern and the inspection protocol;
a scan range automatic setting unit that, after image sensing of a positioning image obtained by image sensing a patient, automatically sets a scan range upon inspection in accordance with the range setting pattern linked to the inspection protocol;
an X-ray source that irradiates the patient with an X-ray;
an X-ray detector, oppositely provided to the X-ray source, that detects the X-ray transmitted through the patient;
a rotary disc, equipped with the X-ray source and the X-ray detector, that rotates around the patient; and
a control part that performs control so as to irradiate the patient with the X-ray from at least one direction to image-sense the positioning image,
wherein the control part sets a range of the X-ray irradiated upon inspection, based on the scan range.

2. The medical image diagnostic device according to claim 1,
wherein the scan range automatic setting unit generates the range setting pattern from an extraction region range including the inspection target and from the margin value, and causes the range setting pattern to be stored in the storage part, prior to the inspection.

3. The medical image diagnostic device according to claim 2, comprising an input part that enables an operator to input the margin value in an arbitrary width with respect to the extraction region range with a GUI.

4. The medical image diagnostic device according to claim 3, comprising a display unit that displays the image-sensed positioning image,
wherein the scan range automatic setting unit performs control so as to display, on the display unit, the positioning image and the range setting pattern based on the margin value inputted from the input unit.

5. The medical image diagnostic device according to claim 4,
wherein the scan range automatic setting unit performs control so as to display, on the display unit, a list of the range setting patterns stored in the storage part.

6. The medical image diagnostic device according to claim 1,
wherein the scan range automatic setting unit reads the margin value corresponding to the inspection target extracted from the positioning image from the storage part, and automatically sets the scan range upon inspection.

7. The medical image diagnostic device according to claim 1,
wherein the storage part stores a map in which a height of a table on which the patient is placed and an image magnification of the positioning image are made to correspond to each other, and
wherein the scan range automatic setting unit refers to the map, and in correspondence with the height of the table upon inspection, adjusts the margin value stored in the range setting pattern, and sets the scan range.

8. The medical image diagnostic device according to claim 1,
wherein the storage part stores a map in which an electrocardiographic waveform of the patient and movement of a heart are made to correspond to each other, and
wherein the scan range automatic setting unit refers to the map based on the electrocardiographic waveform of the patient, obtained upon image sensing of the positioning image, adjusts the margin value stored in the range setting pattern, and sets the scan range.

9. The medical image diagnostic device according to claim 1,
wherein the scan range automatic setting unit calculates an inclination θ of a body axis of the patient with respect to a scan center line from the positioning image, generates a θ-rotated image as an image obtained by θ-rotating the positioning image, generates an extraction region range with respect to the θ-rotated image, calculates a θ-rotated scan range as a scan range with respect to the θ-rotated image, and sets a value obtained by -θ-rotating the θ-rotated scan range as the scan range.

10. The medical image diagnostic device according to claim 1,
wherein the storage part stores a map in which an extraction FOV as an FOV of the extraction region range with respect to the positioning image and a collection FOV as an FOV upon image sensing so as to attain an appropriate BH correction degree are made to correspond to each other, and wherein the scan range automatic setting unit refers to the map, and sets the collection FOV corresponding to the extraction FOV as the scan range.

11. The medical image diagnostic device according to claim 1, wherein when the operator adjusts the scan range, the scan range automatic setting unit accumulates scan range adjustment information in the storage part, and upon next inspection, sets the scan range using a margin value optimized based on the accumulated scan range adjustment information.

12. An image processing method for a medical image diagnostic device having a storage part, an X-ray source, an X-ray detector oppositely provided to the X-ray source, a rotary disc equipped with the X-ray source and the X-ray detector, and a control part, comprising:

linking, to an inspection protocol, a range setting pattern in which an inspection target and a margin value are made to correspond to each other, and storing the range setting pattern and the inspection protocol in the storage part, wherein after image sensing of a positioning image obtained by image sensing a patient, the control part automatically sets a scan range upon inspection in accordance with the range setting pattern linked to the inspection protocol, irradiating the patient with an X-ray from the X-ray source, detecting the X-ray transmitted through a patient with the X-ray detector, rotating the rotary disc around the patient, and performing control so as to irradiate the patient with the X-ray from at least one direction to image-sense the positioning image.

* * * * *